(12) United States Patent
Elisseeff et al.

(10) Patent No.: US 8,946,191 B2
(45) Date of Patent: Feb. 3, 2015

(54) IMIDATED BIOPOLYMER ADHESIVE AND HYDROGEL

(75) Inventors: Jennifer H. Elisseeff, Baltimore, MD (US); Iossif A. Strehin, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 564 days.

(21) Appl. No.: 12/517,672

(22) PCT Filed: Dec. 4, 2007

(86) PCT No.: PCT/US2007/086334
§ 371 (c)(1),
(2), (4) Date: Dec. 15, 2009

(87) PCT Pub. No.: WO2008/070640
PCT Pub. Date: Jun. 12, 2008

(65) Prior Publication Data
US 2010/0137241 A1   Jun. 3, 2010

Related U.S. Application Data

(60) Provisional application No. 60/868,459, filed on Dec. 4, 2006.

(51) Int. Cl.
| | | |
|---|---|---|
| *A61K 31/737* | (2006.01) | |
| *C08F 8/30* | (2006.01) | |
| *A61L 24/00* | (2006.01) | |
| *A61L 24/08* | (2006.01) | |
| *A61L 27/20* | (2006.01) | |
| *A61L 27/34* | (2006.01) | |
| *A61L 27/52* | (2006.01) | |
| *A61L 27/58* | (2006.01) | |
| *A61L 31/04* | (2006.01) | |
| *A61L 31/08* | (2006.01) | |
| *A61L 31/14* | (2006.01) | |
| *C08B 37/00* | (2006.01) | |
| *C08L 5/08* | (2006.01) | |
| *C09J 171/02* | (2006.01) | |
| *C08L 71/02* | (2006.01) | |
| *C08G 65/329* | (2006.01) | |
| *C08G 65/333* | (2006.01) | |
| *C08B 37/08* | (2006.01) | |

(52) U.S. Cl.
CPC ............... *C08F 8/30* (2013.01); *A61L 24/0031* (2013.01); *A61L 24/0042* (2013.01); *A61L 24/08* (2013.01); *A61L 27/20* (2013.01); *A61L 27/34* (2013.01); *A61L 27/52* (2013.01); *A61L 27/58* (2013.01); *A61L 31/042* (2013.01); *A61L 31/08* (2013.01); *A61L 31/145* (2013.01); *A61L 31/148* (2013.01); *C08B 37/0069* (2013.01); *C08L 5/08* (2013.01); *C09J 171/02* (2013.01); *C08L 71/02* (2013.01); *C08G 65/329* (2013.01); *C08G 65/33306* (2013.01); *C08L 2203/02* (2013.01)
USPC .................................. 514/54; 536/53

(58) Field of Classification Search
None
See application file for complete search history.

(56) References Cited

U.S. PATENT DOCUMENTS

| 5,218,069 | A | | 6/1993 | Enomoto et al. | |
|---|---|---|---|---|---|
| 5,298,643 | A | | 3/1994 | Greenwald | |
| 5,436,221 | A | * | 7/1995 | Kitaguchi et al. | 514/19.3 |
| 5,907,028 | A | | 5/1999 | Wardzinska et al. | |
| 6,106,554 | A | * | 8/2000 | Bretton | 623/6.62 |
| 6,962,979 | B1 | * | 11/2005 | Rhee | 530/356 |

FOREIGN PATENT DOCUMENTS

| EP | 0438240 A2 | 7/1991 |
|---|---|---|
| WO | WO-2004/029137 | 4/2004 |

OTHER PUBLICATIONS

Luo et al. Bioconjugate Chem. 2001, 12, 1085-1088.*
Pieper et al. Biomaterials 20 (1999) 847-8.*
Sanborn et al. Biomaterials 32 (2002) 2703-2710.*
Ibim et al., "Poly(anhydride-co-imides): in vivo biocompatibility in a rat model", Biomaterials 19(10): 941-951 (1998).
Attawia et al., "In Vitro Bone Biocompatibility of Poly(anhydride-co-imides) Containing Pyromellitylimidoalanine", Journal of Orthopaedic Research vol. 14, No. 3, pp. 445-454 (1996).
Pumphrey et al., "Neoglycans, Carbodiimide-modified Glycosaminoglycans: A New Class of Anticancer Agents That Inhibit Cancer Cell Proliferation and Induce Apoptosis", Cancer Research, vol. 62, No. 13, pp. 3722-3728 (2002).
Supplemental European Search Report dated Jul. 12, 2011, in corresponding European Patent Application No. 07854909.4.

* cited by examiner

*Primary Examiner* — Layla Bland
(74) *Attorney, Agent, or Firm* — Johns Hopkins Technology Transfer

(57) ABSTRACT

Biologically compatible polymers carry an imide and can be used as an adhesive, a hydrogel or both. A second biologically compatible polymer reactive with the imidated polymer can be used therewith to seal openings.

8 Claims, 20 Drawing Sheets

FIG. 11

IMIDATED BIOPOLYMER ADHESIVE AND HYDROGEL

BACKGROUND OF INVENTION

Naturally derived biopolymers do not always have the structural or functional characteristics required for biomedical applications. Nevertheless, polymeric biomaterials are used in biomedical applications including medical device coatings, artificial implants, and drug delivery devices. Polymer networks may be formed, for example, by crosslinking water soluble polymer solutions to form a water insoluble polymer network. Mechanical and structural properties may be manipulated by modification of the crosslinking density which controls network pore size, water content, and mechanical properties.

Polymers, matrices or gels are attractive for tissue engineering because those materials can encapsulate cells. Some polymers or gels have a high, tissue-like water content enabling nutrient and waste transport.

SUMMARY OF THE INVENTION

In part, the present disclosure provides for a composition comprising at least one monomeric unit of a biologically compatible polymer functionalized with an imide to provide a tissue adhesive, a hydrogel or both.

In another embodiment, at least one of the monomeric units of the biologically compatible polymer is conjugated to a second functional group, which can be an imide. The second functional group, if not an imide, can be any known functional group and can provide directionality to the polymer.

A monomer can be functionalized with at least two functional groups. Overall, when the polymer contains plural species of functional groups, the polymer can contain substantially equal molar amounts of the different functional groups, or the ratios can be varied as a design choice.

Further, the functionalized biologically compatible polymer compositions may comprise at least a second biocompatible polymer that reacts with the first imidated biological polymer. Thus, the second polymer can contain functional groups reactive with an imide or another functional group on the first imidated polymer. The functional group on the second polymer can be, for example, an amine group.

Compositions of the present disclosure may further comprise a biologically active agent, such as a nutrient, a cell, such as a blood cell or a chondrocyte, or an undifferentiated cell, such as a stem cell, such as a hematopoietic stem cell or a mesenchymal stem cell.

In some embodiments, the compositions of interest are hydrogels with adhesive properties.

The instant invention provides a composition comprising a biologically compatible first polymer functionalized with an imide group, and optionally, a bridging molecule, such as a functionalized second polymer, to provide a medical adhesive. In some embodiments, the first polymer comprises at least 10 monomeric units, at least 100 monomeric units or at least 1000 or more units of monomer. The bridging molecule can contain plural functional groups to ensure reaction with at least two molecules of the first polymer.

In a polymer, not all monomers need be functionalized with a reactive moiety.

The first polymer can be reactive with a surface of a structure, such as a biological structure, such as an organ, tissue or cell, such as a cartilage or bone surface, or an artificial structure, such as a prosthesis. A second functional moiety on the first imidated polymer, which may be an imide, also can be reactive with a surface. The first polymer can be reactive with a bridging molecule. The reactions can be through any means that provide a level of adhesion, such as a covalent bond, a physical crosslinking, an ionic crosslinking or other molecular mechanism that affixes the molecules onto the surface, structure or entity reactive therewith, and with the bridging molecule.

In certain embodiments, multiple polymers are reacted together to form a multi-layer polymer structure with exposed surfaces reactive with a surface, such as a tissue and with the bridging molecule. The bridging molecule also can be a multiple layered structure.

Additional features and advantages of the present invention are described in, and will be apparent from the following Detailed Description of the Invention.

BRIEF DESCRIPTION OF THE DRAWINGS

FIGS. 1-20 depict various imides that can be used as reactants to derivatize a monomer or polymer of interest.

DETAILED DESCRIPTION OF THE INVENTION

Figure 1:
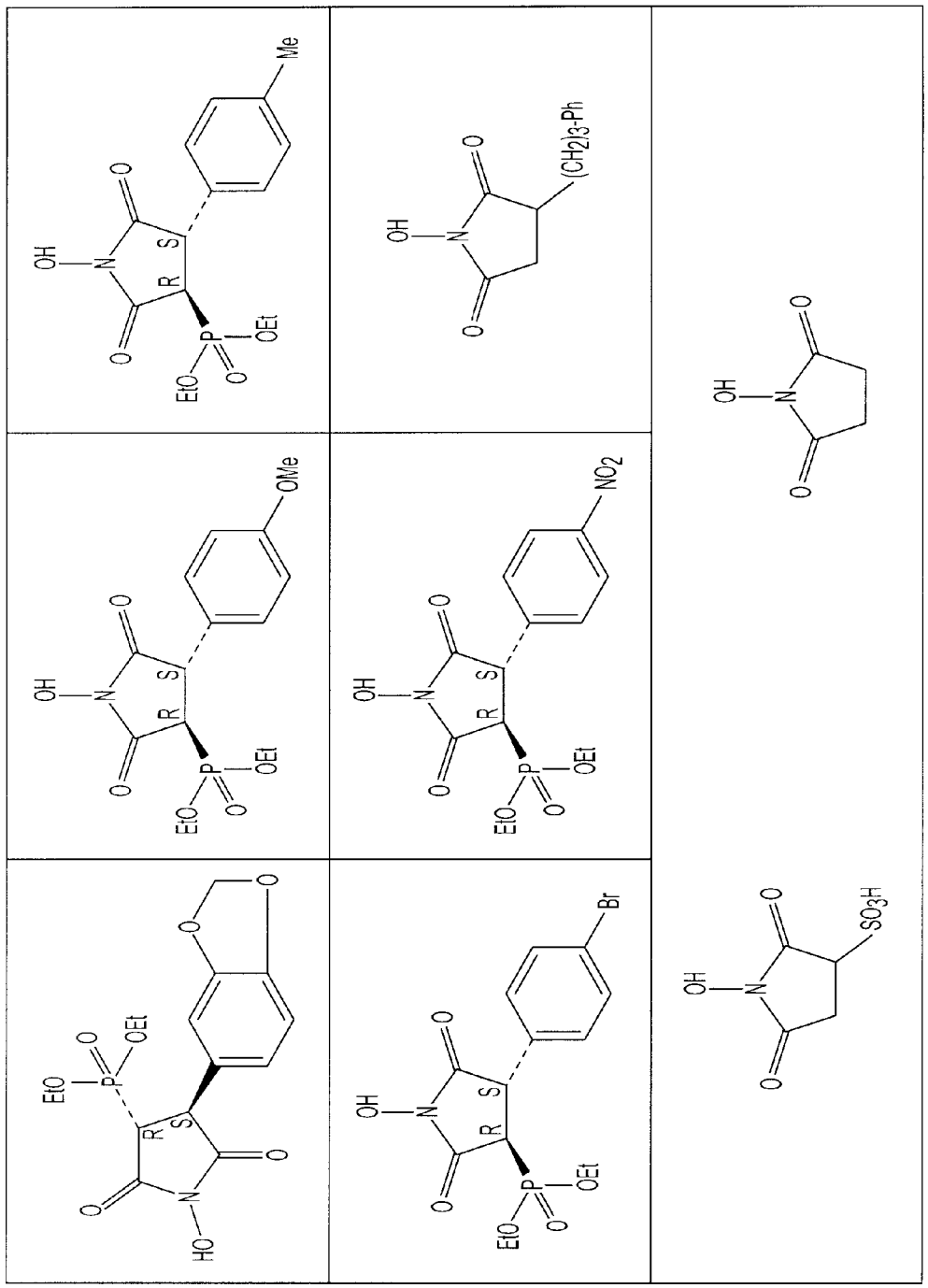

The instant invention relates in part to a method for filling or finishing a defect in a tissue or organ, such as sealing an incision or wound. The method comprises applying to the surface a biologically compatible polymer comprising an imide. Optionally, the surface can first be treated to provide reactive functional groups that can react with a first imidated polymer of interest.

Gels, networks, scaffolds, films and the like of interest made with the composition(s) of interest encourage cell, tissue and organ integration and growth. The optional presence of cells, such as stem cells, enhances cell, tissue and organ integration and growth.

Significant to a product of interest is the enhanced integration with the surrounding tissue to increase stability and bonding to a biological surface and to formation of new tissue. In vitro studies have proven efficacy of the chemical mechanism of reacting to the surface and the increased mechanical strength of the material-cell/tissue/organ interface.

The instant invention addresses the problem of fibrocartilage formation in a surgical method. The instant invention is usable, for example, in early osteoarthritic joints by using patches and gels to prevent enzymatic synovial degradation during and after implantation. The instant invention also enables marrow stimulation without disrupting subchondral bone integrity. The compound or compounds of interest can be used, for example, in the eye, in the spine, in the musculoskeletal system, at sites carrying cartilage and so on.

The instant invention provides for in situ polymerization techniques to form scaffolds and so on that can be molded to take the desired shape of the defect, promote tissue development by stimulating native cell repair, and can be potentially implanted by minimally invasive injection.

This disclosure is directed, at least in part, to polymers, matrices, and gels, and methods of making and using matrices, polymers and gels. One of said such polymers comprises an imide.

For example, this disclosure provides for functionalized biologically compatible first polymer, such as hyaluronate, keratan sulfate, chondroitin sulfate and the like, substituted with an imide. See WO2006089119, WO2004029137, WO2006105161 and WO2006036681, for example, herein incorporated by reference in entirety, for various uses of similar but unrelated compounds. Either imides are not taught therein or there is an explicit teaching away from the use of imides.

A biological surface refers to an external, environmentally exposed portion of a biological material or entity, such as a microbe, virus, cell, tissue, organ and the like to which a biologically compatible polymer can interact, react and/or adhere thereto.

A biologically compatible polymer refers to a polymer which is functionalized to serve as a composition for applying to a surface. The polymer is one that is a naturally occurring polymer or one that is not toxic to the host. The polymer contains at least an imide. The polymer may be a homopolymer where all monomers are the same or a heteropolymer containing two or more kinds of monomers. The terms "biocompatible polymer", "biocompatible cross-linked polymer matrix" and "biocompatibility" when used in relation to the instant polymers are art-recognized and are considered equivalent to one another, including, to biologically compatible polymer. For example, biocompatible polymers include polymers that are neither toxic to the host (e.g., an animal or human), nor degrade (if the polymer degrades) at a rate that produces monomeric or oligomeric subunits or other byproducts at toxic concentrations in the host.

An active agent and a biologically active agent are used interchangeably herein to refer to a chemical or biological compound that induces a desired pharmacological and/or physiological effect, wherein the effect may be prophylactic or therapeutic. The terms also encompass pharmaceutically acceptable, pharmacologically active derivatives of those active agents specifically mentioned herein, including, but not limited to, salts, esters, amides, prodrugs, active metabolites, analogs and the like. When the terms "active agent," "pharmacologically active agent" and "drug" are used, then, it is to be understood that the invention includes the active agent per se as well as pharmaceutically acceptable, pharmacologically active salts, esters, amides, prodrugs, metabolites, analogs etc. The active agent can be a biological entity, such as a virus or cell, whether naturally occurring or manipulated, such as transformed.

Biocompatible polymer, biocompatible cross-linked polymer matrix and biocompatibility are art-recognized. For example, biocompatible polymers include polymers that are neither themselves toxic to the host (e.g., an animal or human), nor degrade (if the polymer degrades) at a rate that produces monomeric or oligomeric subunits or other byproducts at toxic concentrations in the host. In certain embodiments of the present invention, biodegradation generally involves degradation of the polymer in an organism, e.g., into its monomeric subunits, which may be known to be effectively non-toxic. Intermediate oligomeric products resulting from such degradation may have different toxicological properties, however, or biodegradation may involve oxidation or other biochemical reactions that generate molecules other than monomeric subunits of the polymer. Consequently, in certain embodiments, toxicology of a biodegradable polymer intended for in vivo use, such as implantation or injection into a patient, may be determined after one or more toxicity analyses. It is not necessary that any subject composition have a purity of 100% to be deemed biocompatible; indeed, it is only necessary that the subject compositions be biocompatible as set forth above. Hence, a subject composition may comprise polymers comprising 99%, 98%, 97%, 96%, 95%, 90%, 85%, 80%, 75% or even less of biocompatible polymers, e.g., including polymers and other materials and excipients described herein, and still be biocompatible.

To determine whether a polymer or other material is biocompatible, it may be necessary to conduct a toxicity analysis. Such assays are well known in the art. One example of such an assay may be performed with live cells, such as HeLa, 293, CHO and the like. The sample is partially or completely degraded as known in the art, using, for example, chemical means or enzymatic means. An aliquot of the treated sample products are placed in culture plates previously seeded with the cells. The sample products are incubated with the cells. The results of the assay may be plotted as % relative growth vs. concentration of degraded sample.

In addition, monomers, polymers, polymer matrices, and formulations of the present invention may also be evaluated by well-known in vivo tests, such as subcutaneous implantations in rats to confirm that they do not cause significant levels of irritation or inflammation at the subcutaneous implantation sites.

Biodegradable is art-recognized, and includes monomers, polymers, polymer matrices, gels, compositions and formulations, such as those described herein, that are intended to degrade during use, such as in vivo. Biodegradable polymers and matrices typically differ from non-biodegradable polymers in that the former may be degraded during use. In certain embodiments, such use involves in vivo use, such as in vivo therapy, and in other certain embodiments, such use involves in vitro use. In general, degradation attributable to biodegradability involves the degradation of a biodegradable polymer into its component subunits, or digestion, e.g., by a biochemical process, of the polymer into smaller, non-polymeric subunits. In certain embodiments, two different types of biodegradation may generally be identified. For example, one type of biodegradation may involve cleavage of bonds (whether covalent or otherwise) in the polymer backbone. In such biodegradation, monomers and oligomers typically result, and even more typically, such biodegradation occurs by cleavage of a bond connecting one or more of subunits of a polymer. In contrast, another type of biodegradation may involve cleavage of a bond (whether covalent or otherwise) internal to a side chain or that connects a side chain, functional group and so on to the polymer backbone. For example, a therapeutic agent, biologically active agent, or other chemical moiety attached as a side chain to the polymer backbone may be released by biodegradation. In certain embodiments, one or the other or both general types of biodegradation may occur during use of a polymer. As used herein, the term "biodegradation" encompasses both general types of biodegradation.

The degradation rate of a biodegradable polymer often depends in part on a variety of factors, including the chemical identity of the linkage responsible for any degradation, the molecular weight, crystallinity, biostability, and degree of cross-linking of such polymer, the physical characteristics of the implant, shape and size, and the mode and location of administration. For example, the greater the molecular weight, the higher the degree of crystallinity, and/or the greater the biostability, the biodegradation of any biodegradable polymer is usually slower. The term "biodegradable" is intended to cover materials and processes also termed "bioerodible".

In certain embodiments, the biodegradation rate of such polymer may be characterized by the presence of enzymes, for example, a chondroitinase. In such circumstances, the biodegradation rate may depend on not only the chemical identity and physical characteristics of the polymer matrix, but also on the identity of any such enzyme.

In certain embodiments, polymeric formulations of the present invention biodegrade within a period that is acceptable in the desired application. In certain embodiments, such as in vivo therapy, such degradation occurs in a period usually less than about five years, one year, six months, three months, one month, fifteen days, five days, three days, or even one day on exposure to a physiological solution with a pH between 6 and 8 having a temperature of between about 25 and 37° C. In other embodiments, the polymer degrades in a period of between about one hour and several weeks, depending on the desired application. In some embodiments, the polymer or polymer matrix may include a detectable agent that is released on degradation.

Cross-linked herein refers to a composition containing intermolecular cross-links and optionally intramolecular cross-links, arising from, generally, the formation of covalent bonds. Covalent bonding between two cross-linkable components may be direct, in which case an atom in one component is directly bound to an atom in the other component, or it may be indirect, through a linking group. A cross-linked gel or polymer matrix may, in addition to covalent bonds, also include intermolecular and/or intramolecular noncovalent bonds such as hydrogen bonds and electrostatic (ionic) bonds.

Functionalized refers to a modification of an existing molecular segment or group to generate or to introduce a new reactive or more reactive group (e.g., imide group) that is capable of undergoing reaction with another functional group (e.g., an amine group) to form a covalent bond. For example, carboxylic acid groups can be functionalized by reaction with a carbodiimide and an imide reagent using known procedures to provide a new reactive functional group in the form of an imide group substituting for the hydrogen in the hydroxyl group of the carboxyl function.

Gel refers to a state of matter between liquid and solid, and is generally defined as a cross-linked polymer network swollen in a liquid medium. Typically, a gel is a two-phase colloidal dispersion containing both solid and liquid, wherein the amount of solid is greater than that in the two-phase colloidal dispersion referred to as a "sol." As such, a "gel" has some of the properties of a liquid (i.e., the shape is resilient and deformable) and some of the properties of a solid (i.e., the shape is discrete enough to maintain three dimensions on a two-dimensional surface.)

"Gelation time," also referred to herein as "gel time," refers to the time it takes for a composition to become non-flowable under modest stress. This is generally exhibited as reaching a physical state in which the elastic modulus, G', equals or exceeds the viscous modulus, G", i.e., when tan(delta) becomes 1 (as may be determined using conventional rheological techniques).

A hydrogel is a water-swellable polymeric matrix that can absorb water to form elastic gels, wherein "matrices" are three-dimensional networks of macromolecules held together by covalent or noncovalent crosslinks. On placement in an aqueous environment, dry hydrogels swell by the acquisition of liquid therein to the extent allowed by the degree of cross-linking.

Hydrogels consist of hydrophilic polymers cross-linked to from a water-swollen, insoluble polymer network. Cross-linking can be initiated by many physical or chemical mechanisms. Photopolymerization is a method to covalently crosslink polymer chains, whereby a photoinitiator and polymer solution (termed "pre-gel" solution) are exposed to a light source specific to the photoinitiator. On activation, the photoinitiator reacts with specific functional groups in the polymer chains, crosslinking them to form the hydrogel. The reaction is rapid (3-5 minutes) and proceeds at room and body temperature. Photoinduced gelation enables spatial and temporal control of scaffold formation, permitting shape manipulation after injection and during gelation in vivo. Cells and bioactive factors can be easily incorporated into the hydrogel scaffold by simply mixing with the polymer solution prior to photogelation.

Alternatively, the reactants can contain complementary reactive groups, such as an imide and an amine, that yield cross-linking without the need of an external initiator.

Hydrogels of interest can be semi-interpenetrating networks that promote cell, tissue and organ repair while discouraging scar formation. The hydrogels of interest are derivatized to contain an imide to be reactive with a surface and/or the second polymer of interest. Hydrogels of interest also are configured to have a viscosity that will enable the gelled hydrogel to remain affixed on or in the cell, tissue or organ, or surface. Viscosity can be controlled by the monomers and polymers used, by the level of water trapped in the hydrogel and by incorporated thickeners, such as biopolymers, such as proteins, lipids, saccharides and the like. An example of such a thickener is hyaluronic acid or collagen.

Polymer is used to refer to molecules composed of repeating monomer units, including homopolymers, block copolymers, heteropolymers, random copolymers, graft copolymers and so on. "Polymers" also include linear polymers as well as branched polymers, with branched polymers including highly branched, dendritic, and star polymers.

A monomer is the basic repeating unit in a polymer. A monomer may itself be a monomer or may be dimer or oligomer of at least two different monomers, and each dimer or oligomer is repeated in a polymer.

A polymerizing initiator refers to any substance that can initiate polymerization of monomers or macromers by, for example, free radical generation. The polymerizing initiator often is an oxidizing agent. Exemplary polymerizing initiators include those which are activated by exposure to, for example, electromagnetic radiation or heat.

Incorporated, encapsulated and entrapped are art-recognized when used in reference to a therapeutic agent, dye, or other material and a polymeric composition, such as a composition of the present invention. In certain embodiments, these terms include incorporating, formulating or otherwise including such agent into a composition that allows for sustained release of such agent in the desired application. The terms may contemplate any manner by which a therapeutic agent or other material is incorporated into a polymer matrix, including, for example, attached to a monomer of such polymer (by covalent or other binding interaction) and having such monomer be part of the polymerization to give a polymeric formulation, distributed throughout the polymeric matrix, appended to the surface of the polymeric matrix (by covalent or other binding interactions), encapsulated inside the polymeric matrix, etc. The term "co-incorporation" or "co-encapsulation" refers to the incorporation of a therapeutic agent or other material and at least one other therapeutic agent or other material in a subject composition.

More specifically, the physical form in which any therapeutic agent or other material is encapsulated in polymers may vary with the particular embodiment. For example, a therapeutic agent or other material may be first encapsulated in a microsphere and then combined with the polymer in such a way that at least a portion of the microsphere structure is maintained. Alternatively, a therapeutic agent or other material may be sufficiently immiscible in the polymer of the invention that it is dispersed as small droplets, rather than being dissolved, in the polymer. Any form of encapsulation or incorporation is contemplated by the present invention, in so much as the sustained release of any encapsulated therapeutic agent or other material determines whether the form of encapsulation is sufficiently acceptable for any particular use.

Treating or treatment is an art-recognized term which includes curing as well as ameliorating at least one symptom of any condition or disease. Treating includes preventing a disease, disorder or condition from occurring in an animal which may be predisposed to the disease, disorder and/or condition but has not yet been diagnosed as having it; inhibiting the disease, disorder or condition, e.g., impeding its progress; and relieving the disease, disorder or condition, e.g., causing any level of regression of the disease, disorder preventing a disease, disorder or condition from occurring in an animal which may be predisposed to the disease, disorder and/or condition but has not yet been diagnosed as having it; inhibiting the disease, disorder or condition, e.g., impeding its progress; and relieving the disease, disorder or condition, e.g., causing regression of the disease, disorder and/or condition. Further, treating the disease or condition includes ameliorating at least one symptom of the particular disease or condition, even if the underlying pathophysiology is not affected or other symptoms remain at the same level.

Pharmaceutically acceptable salts are art-recognized, and include relatively non-toxic, inorganic and organic acid addition salts of compositions of the present invention, including without limitation, therapeutic agents, excipients, other materials and the like. Examples of pharmaceutically acceptable salts include those derived from mineral acids, such as hydrochloric acid and sulfuric acid, and those derived from organic acids, such as ethanesulfonic acid, benzenesulfonic acid, p-toluenesulfonic acid, and the like. Examples of suitable inorganic bases for the formation of salts include the hydroxides, carbonates, and bicarbonates of ammonia, sodium, lithium, potassium, calcium, magnesium, aluminum, zinc and the like. Salts may also be formed with suitable organic bases, including those that are non-toxic and strong enough to form such salts. For purposes of illustration, the class of such organic bases may include mono-, di-, and trialkylamines, such as methylamine, dimethylamine, and triethylamine; mono-, di- or trihydroxyalkylamines such as mono-, di-, and triethanolamine; amino acids, such as arginine and lysine; guanidine; N-methylglucosamine; N-methylglucamine; L-glutamine; N-methylpiperazine; morpholine; ethylenediamine; N-benzylphenethylamine; (trihydroxymethyl) aminoethane; and the like, see, for example, J. Pharm. Sci., 66: 1-19 (1977).

Prophylactic or therapeutic treatment is art-recognized and includes administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if it is administered after manifestation of the unwanted condition, the treatment is therapeutic (i.e., it is intended to diminish, ameliorate, or stabilize the existing unwanted condition or side effects thereof).

The term "aliphatic" is an art-recognized term and includes linear, branched, and cyclic alkanes, alkenes or alkynes. In certain embodiments, aliphatic groups in the present invention are linear or branched and have from 1 to about 20 carbon atoms.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer carbon atoms. Likewise, cycloalkyls have from about 3 to about 10 carbon atoms in their ring structure, and alternatively about 5, 6 or 7 carbons in the ring structure.

Moreover, the term "alkyl" (or "lower alkyl") includes both "unsubstituted alkyls" and "substituted alkyls", the latter of which refers to alkyl moieties having substituents replacing a hydrogen on one or more carbons of the hydrocarbon backbone. Such substituents may include, for example, a halogen, a hydroxyl, a carbonyl (such as a carboxyl, an alkoxycarbonyl, a formyl or an acyl), a thiocarbonyl (such as a thioester, a thioacetate, or a thioformate), an alkoxyl, a phosphoryl, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain may themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls may be further substituted with alkyls, alkenyls, alkoxys, alkylthios, aminoalkyls, carbonyl-substituted alkyls, —$CF_3$, —CN and the like.

The term "aralkyl" is art-recognized, and includes aryl groups (e.g., an aromatic or heteroaromatic group).

The terms "alkenyl" and "alkynyl" are art-recognized, and include unsaturated aliphatic groups analogous in length and possible substitution to the alkyls described above, but that contain at least one double or triple bond, respectively.

The term "heteroatom" is art-recognized, and in an organic molecule, generally includes an atom of any element other than carbon or hydrogen. Illustrative heteroatoms include boron, nitrogen, oxygen, phosphorus, sulfur and selenium.

The term "aryl" is art-recognized, and includes 5-, 6- and 7-membered single ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring may be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocyclyls, or rings joined by non-cyclic moieties.

The terms "ortho", "meta" and "para" are art-recognized and apply to 1,2-, 1,3- and 1,4-disubstituted cyclohexanes, respectively. For example, the names 1,2-dimethylbenzene and ortho-dimethylbenzene are synonymous.

The terms "heterocyclyl" and "heterocyclic group" are art-recognized, and include 3- to about 10-membered ring structures, such as 3- to about 7-membered rings, whose ring structures include one to four heteroatoms. Heterocycles may also be polycycles. Heterocyclyl groups include, for example, thiophene, thianthrene, furan, pyran, isobenzofuran, chromene, xanthene, phenoxanthin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones and the like. The heterocyclic ring may be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN or the like.

The terms "polycyclyl" and "polycyclic group" are art-recognized, and include structures with two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms, e.g., three or more atoms are common to both rings, are termed "bridged" rings. Each of the rings of the polycycle may be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN or the like.

The term "carbocycle" is art recognized and includes an aromatic or non-aromatic ring in which each atom of the ring is carbon. The following art-recognized terms have the following meanings: "nitro" means —$NO_2$; the term "halogen" designates —F, —Cl, —Br or —I; the term "sulfhydryl" means —SH; the term "hydroxyl" or "hydroxy" means —OH; and the term "sulfonyl" means —$SO_2$—.

The terms "amine" and "amino" are art-recognized and include both unsubstituted and substituted amines. A primary amine carries two hydrogens, a secondary amine, one hydrogen and another substituent and a tertiary amine, the two hydrogens are substituted. The substituents for one or both of the hydrogens can be, for example, an alkyl, an alkenyl, an aryl, a cycloalkyl, a cycloalkenyl, a heterocycle, a polycycle and so on. If both hydrogens are substituted with carbonyls, the carbonyl framed nitrogen forms an imide.

The term "alkylamine" includes an amine group, as defined above, having a substituted or unsubstituted alkyl attached thereto.

The term "amido" is art-recognized as an amino-substituted carbonyl.

The term "alkylthio" is art-recognized and includes an alkyl group, as defined above, having a sulfur radical attached thereto. In certain embodiments, the "alkylthio" moiety is represented by one of —S-alkyl, —S-alkenyl, —S-alkynyl and so on. Representative alkylthio groups include methylthio, ethylthio and the like.

The term "carbonyl" is art-recognized and includes a C=O structure. Carbonyls are involved in esters; carboxyl groups; formates; thiocarbonyls; thioesters; thiocarboxylic acids; thioformates; ketones; and aldehydes.

The terms "alkoxyl" and "alkoxy" are art-recognized and include an alkyl group, as defined above, having an oxygen radical attached thereto. Representative alkoxyl groups include methoxy, ethoxy, propyloxy, tert-butoxy and the like.

An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl and so on.

The term "sulfonate" is art-recognized and includes a moiety wherein a sulfur atom carries two double bonded oxygens and a single bonded oxygen.

The term "sulfate" is art-recognized and includes a moiety that resembles a sulfonate but includes two single bonded oxygens.

The terms "sulfonamide," "sulfamoyl," "sulfonyl" and "sulfoxido" are art-recognized and each can include a variety of R group substituents as described herein.

The terms "phosphoramidite" and "phosphonamidite" are art-recognized.

The term "selenoalkyl" is art-recognized and includes an alkyl group having a substituted seleno group attached thereto. Exemplary "selenoethers" which may be substituted on the alkyl are selected from one of —Se-alkyl, —Se-alkenyl, —Se-alkynyl and so on.

Substitutions may be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

A hydrocarbon is an art recognized term and includes all permissible compounds having at least one hydrogen and one carbon atom. For example, permissible hydrocarbons include acyclic and cyclic, branched and unbranched, carbocyclic and heterocyclic, aromatic and nonaromatic organic compounds that may be substituted or unsubstituted.

The phrase "protecting group" is art-recognized and includes temporary substituents that protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed, Greene et al., Protective Groups in Organic Synthesis 2nd ed., Wiley, New York, (1991), for example.

The definition of each expression, e.g. alkyl, aryl etc., when it occurs more than once in any structure, is intended to be independent of its definition elsewhere in the same structure unless otherwise indicated expressly or by the context.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, and Ms are art-recognized and represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the Journal of Organic Chemistry; this list is typically presented in a table entitled Standard List of Abbreviations.

Certain monomeric subunits of the present invention may exist in particular geometric or stereoisomeric forms. In addition, polymers and other compositions of the present invention may also be optically active. The present invention contemplates all such compounds, including cis-isomers and trans-isomers, R-enantiomers and S-enantiomers, diastereomers, (d)-isomers, (l)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

It will be understood that substitution or substituted with includes the implicit proviso that such substitution is in accordance with the permitted valency of the substituted atom and the substituent, and that the substitution results in a stable compound, e.g., which does not spontaneously undergo transformation, such as by rearrangement, cyclization, elimination, or other reaction.

The term substituted is also contemplated to include all permissible substituents of organic compounds such as the imide reagent of interest. In a broad aspect, the permissible substituents include acyclic and cyclic, branched and unbranched, carbocyclic and heterocyclic, aromatic and non-aromatic substituents of organic compounds. Illustrative substituents include, for example, those described hereinabove. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

For purposes of this invention, the chemical elements are identified in accordance with the Periodic Table of the Elements, CAS version, Handbook of Chemistry and Physics, 67th Ed., 1986-87.

A functional group or a moiety which can be used for substitution is one capable of mediating formation of a polymer or reaction with a surface or other molecule. Functional groups include the various radicals and chemical entities taught herein, and include alkenyl moieties such as acrylates, methacrylates, dimethacrylates, oligoacrylates, oligomethacrylates, ethacrylates, itaconates or acrylamides. Further functional groups include aldehydes. Other functional groups may include ethylenically unsaturated monomers including, for example, alkyl esters of acrylic or methacrylic acid such as methyl methacrylate, ethyl methacrylate, butyl methacrylate, ethyl acrylate, butyl acrylate, hexyl acrylate, n-octyl acrylate, lauryl methacrylate, 2-ethylhexyl methacrylate, nonyl acrylate, benzyl methacrylate, the hydroxyalkyl esters of the same acids such as 2-hydroxyethyl acrylate, 2-hydroxyethyl methacrylate, and 2-hydroxypropyl methacrylate, the nitrile and amides of the same acids such as acrylonitrile, methacrylonitrile, and methacrylamide, vinyl acetate, vinyl propionate, vinylidene chloride, vinyl chloride, and vinyl aromatic compounds such as styrene, t-butyl styrene and vinyl toluene, dialkyl maleates, dialkyl itaconates, dialkyl methylene-malonates, isoprene and butadiene. Suitable ethylenically unsaturated monomers containing carboxylic acid groups include acrylic monomers such as acrylic acid, methacrylic acid, ethacrylic acid, itaconic acid, maleic acid, fumaric acid, monoalkyl itaconate including monomethyl itaconate, monoethyl itaconate, and monobutyl itaconate, monoalkyl maleate including monomethyl maleate, monoethyl maleate, and monobutyl maleate, citraconic acid and styrene carboxylic acid. Suitable polyethylenically unsaturated monomers include butadiene, isoprene, allylmethacrylate, diacrylates of alkyl diols such as butanediol diacrylate and hexanediol diacrylate, divinyl benzene and the like.

In some embodiments, a monomeric unit of a biologically compatible polymer may be functionalized through one or more thio, carboxylic acid or alcohol moieties located on a monomer of the biopolymer. For example, in the case of chondroitin sulfate, a carbonyl group can be derivatized with a imide group using, for example, carbodiimide chemistry. An alcohol group can be derivatized using, for example, the Mitsunobu reaction, Procter et al., Tetra. Lett. 47(29) 5151-5154, 2006.

In some embodiments, this disclosure is directed to a composition comprising at least one monomeric unit of a biologically compatible polymer, such as hyaluronic acid, heparin sulfate, keratan sulfate and the like, functionalized by an imide. Those starting molecules are natural components of extracellular matrices. However, in general, any biologically compatible polymer can be used as the polymer, which polymer carries at least an imide. Other suitable polymers include those which are naturally occurring, such as a GAG, mucopolysaccharide, collagen or proteoglycan components, such as hyaluronic acid, heparin sulfate, glucosamines, dermatans, keratans, heparans, hyalurunan, aggrecan and the like.

In some embodiments, this disclosure is directed to a composition comprising at least one monomeric unit of a saccharide or other biocompatible monomer or polymer, wherein the monomers have reactive sites that will enable at least inclusion of an imide and other functional groups, such as chondroitin sulfate. Chondroitin sulfate is a natural component of cartilage and may be a useful scaffold material for regeneration. Chondroitin sulfate includes members of 10-60 kDa glycosaminoglycans. The repeat units, or monomeric units, of chondroitin sulfate consist of a disaccharide, β(1→4)-linked D-glucuronyl β(1→3) N-acetyl-D-galactosamine sulfate.

Figure 2:
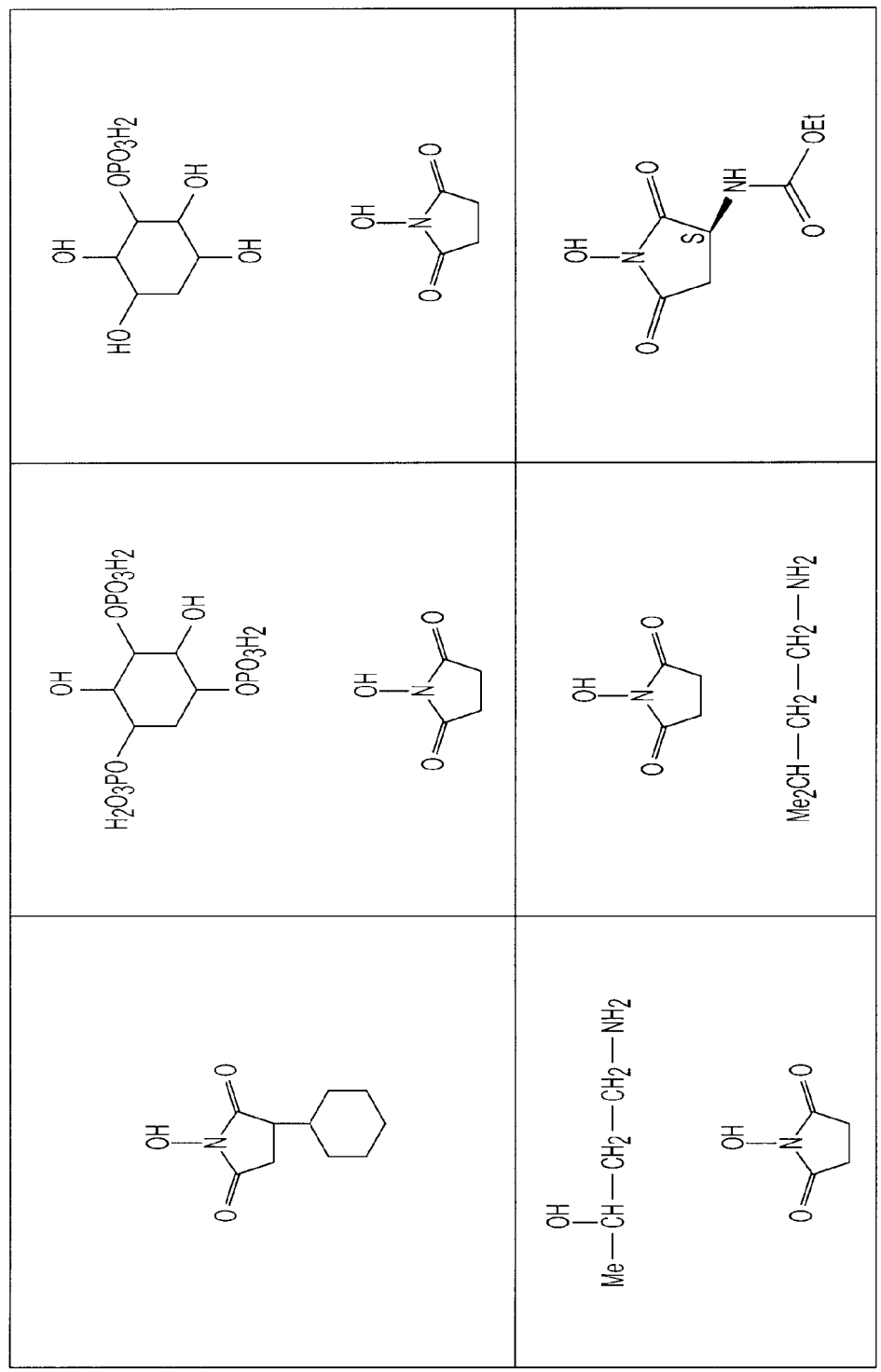
Figure 3:
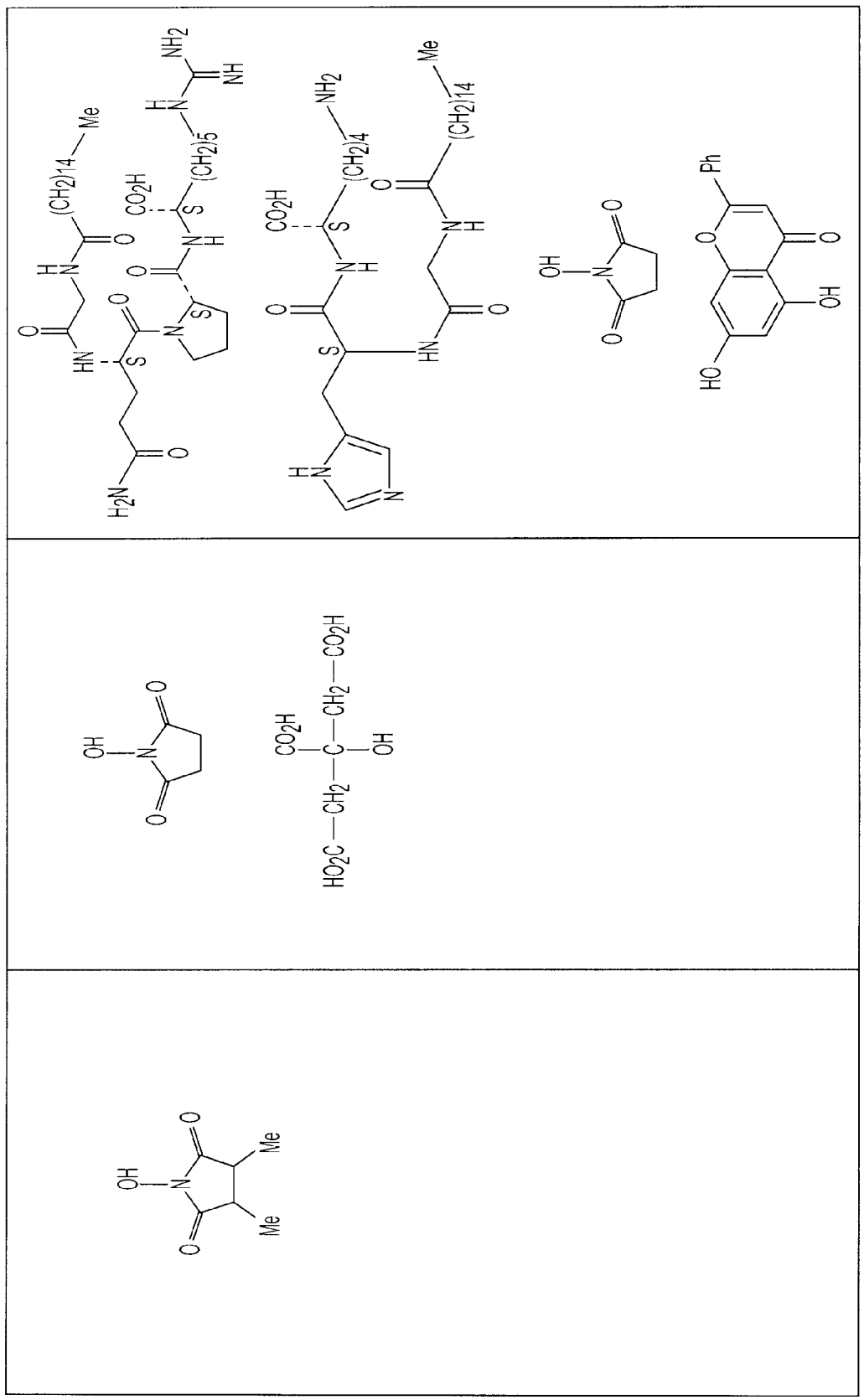
Figure 4:
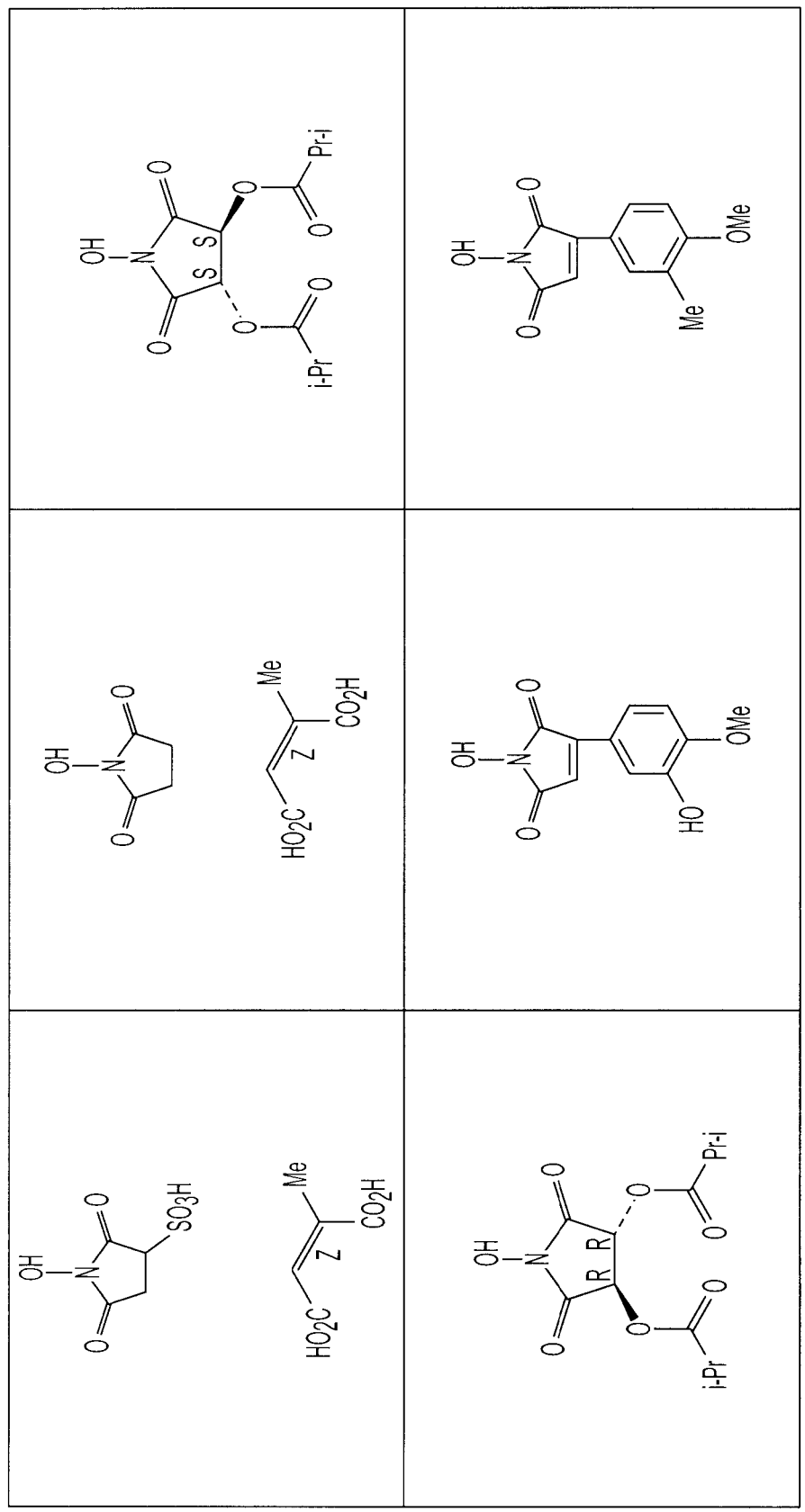
Figure 5:
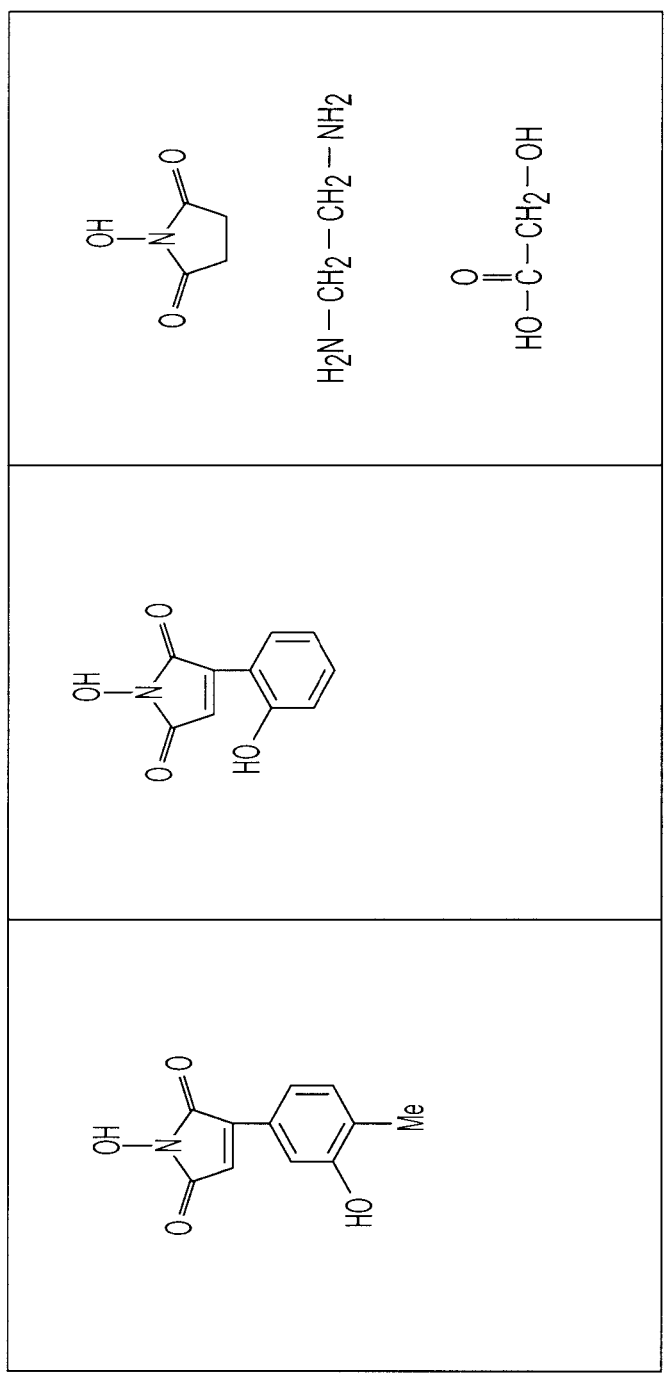
Figure 6:
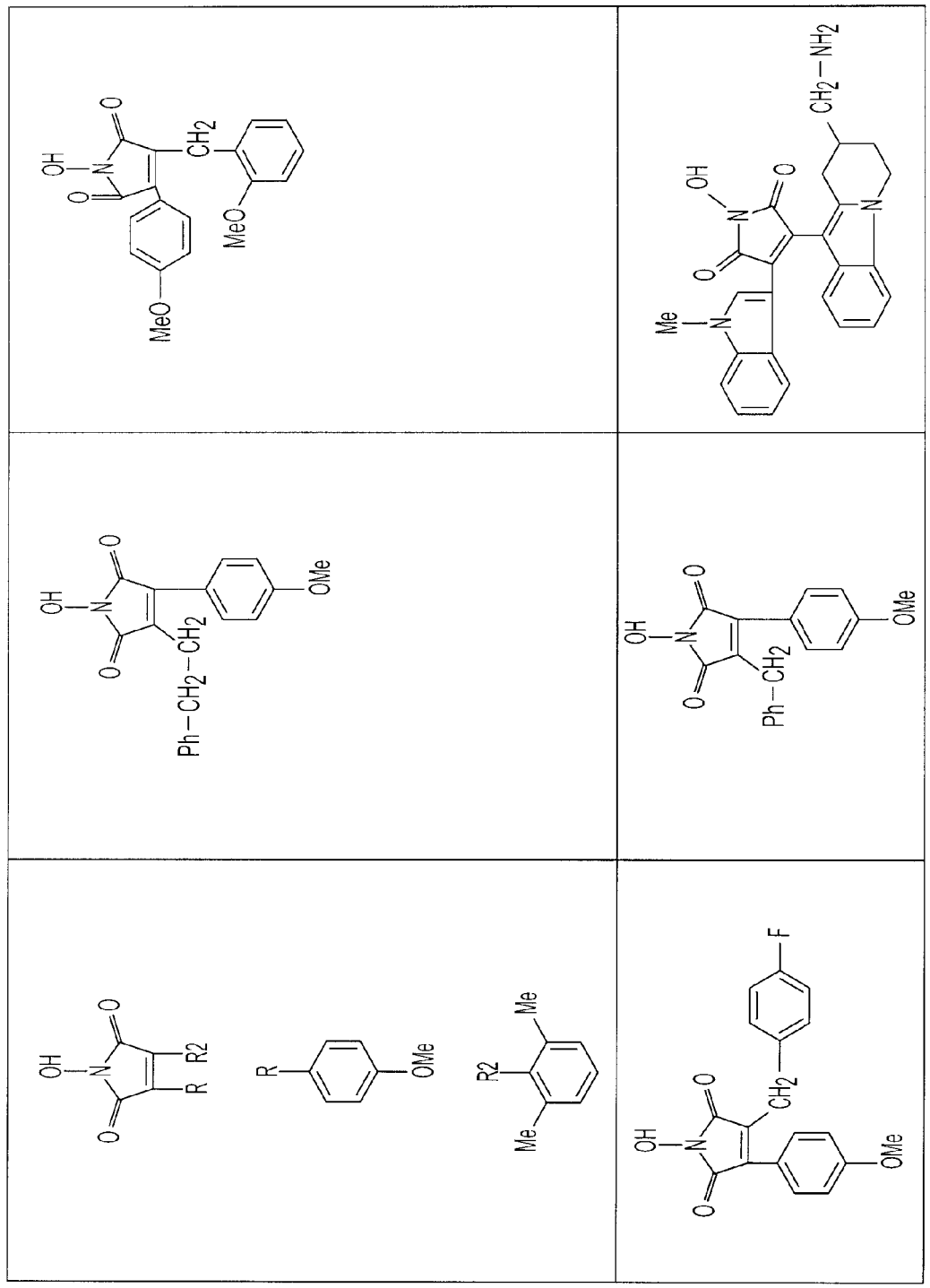
Figure 7:
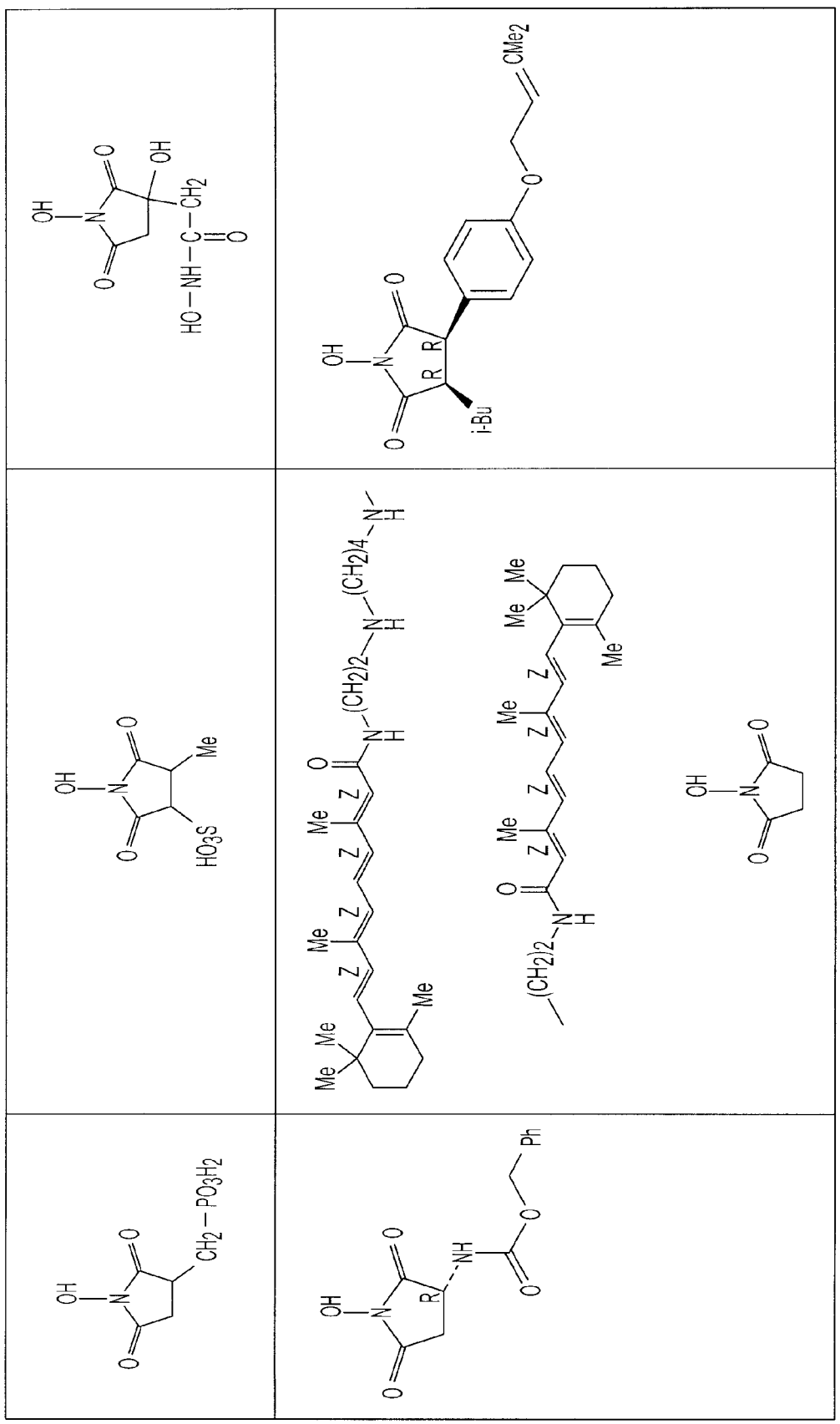
Figure 8:
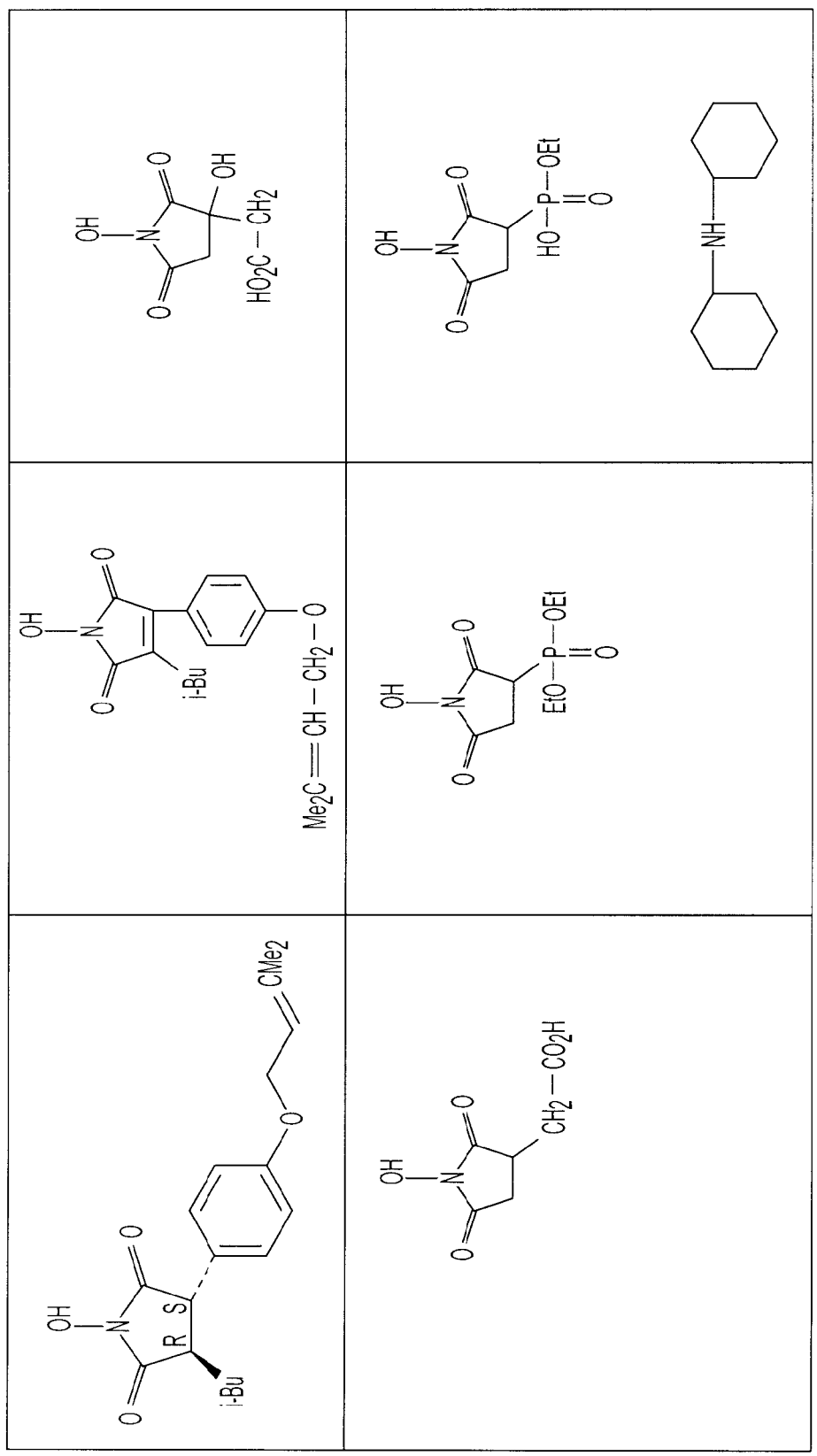
Figure 9:
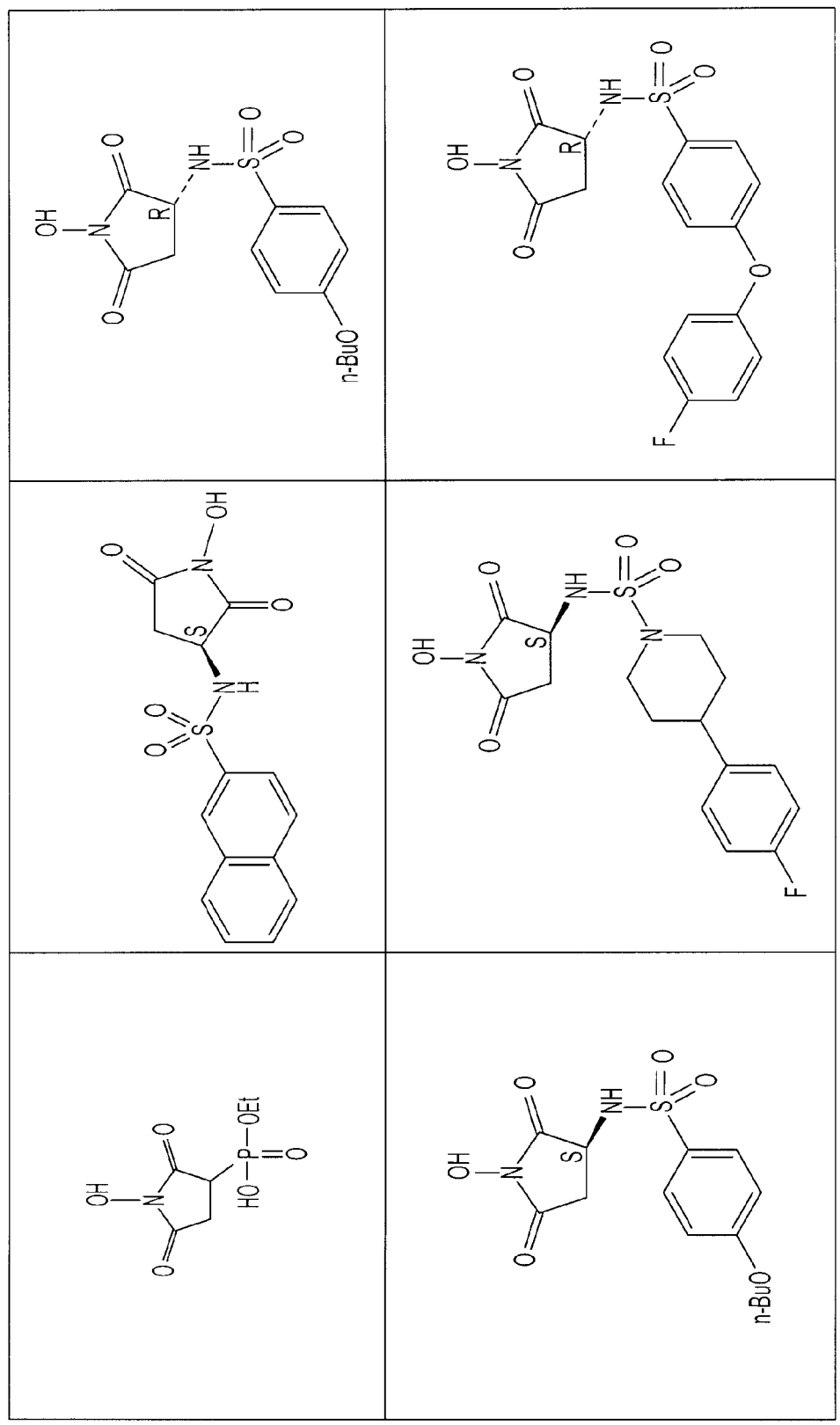
Figure 10:
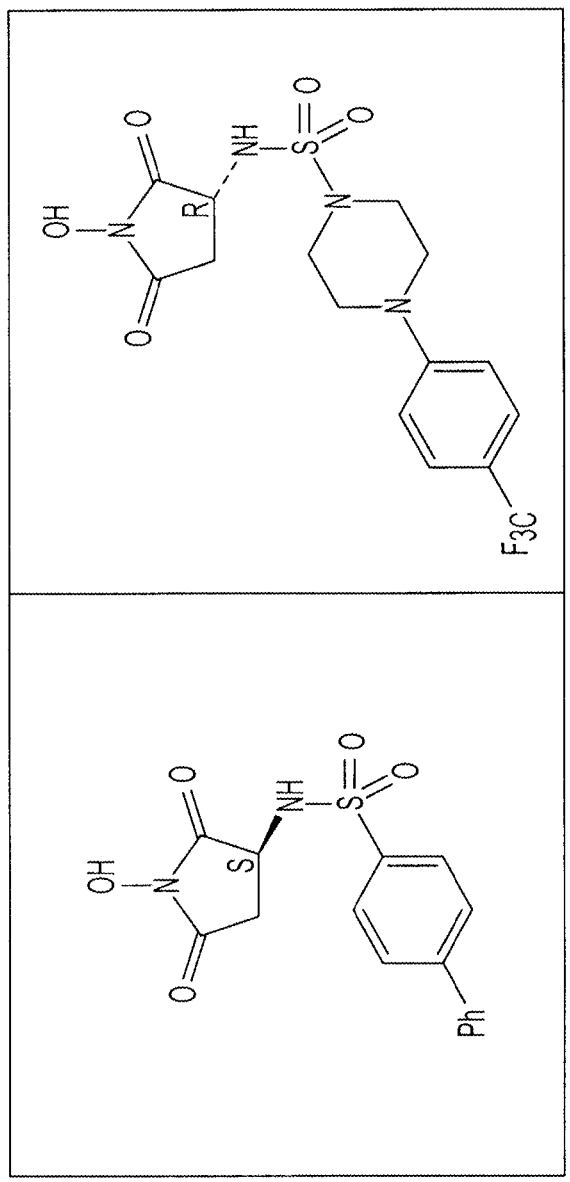
Figure 12:
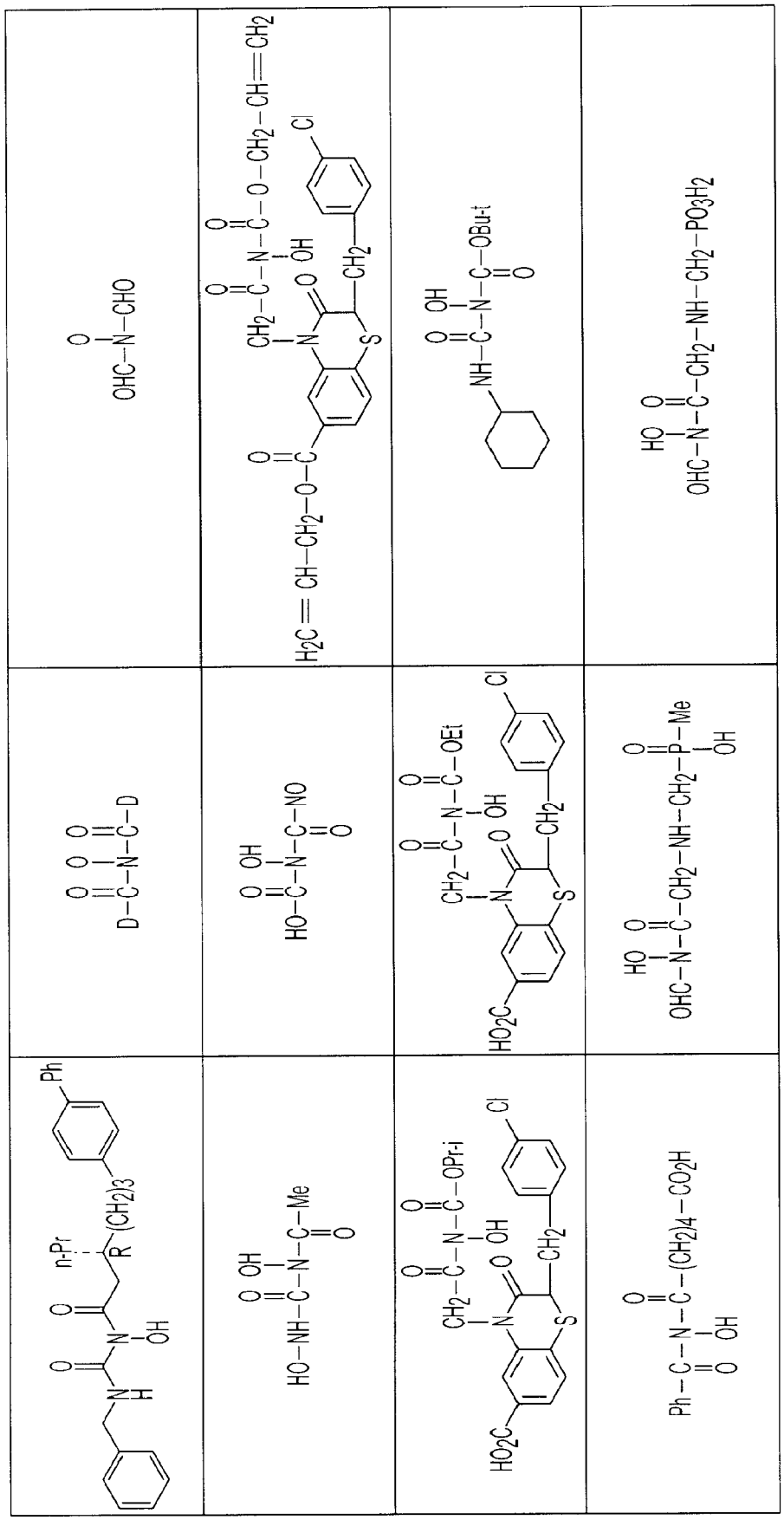
Figure 13:
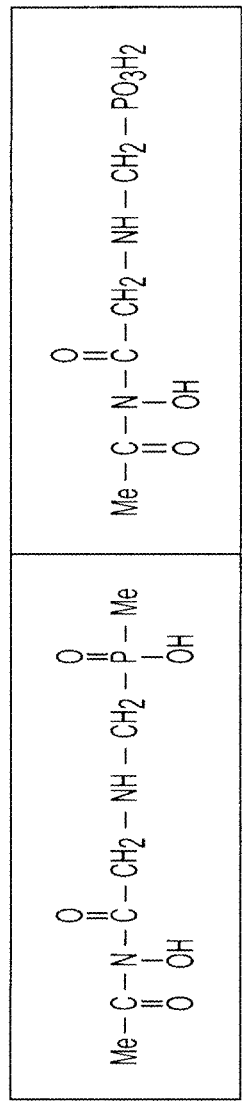
Figure 14:
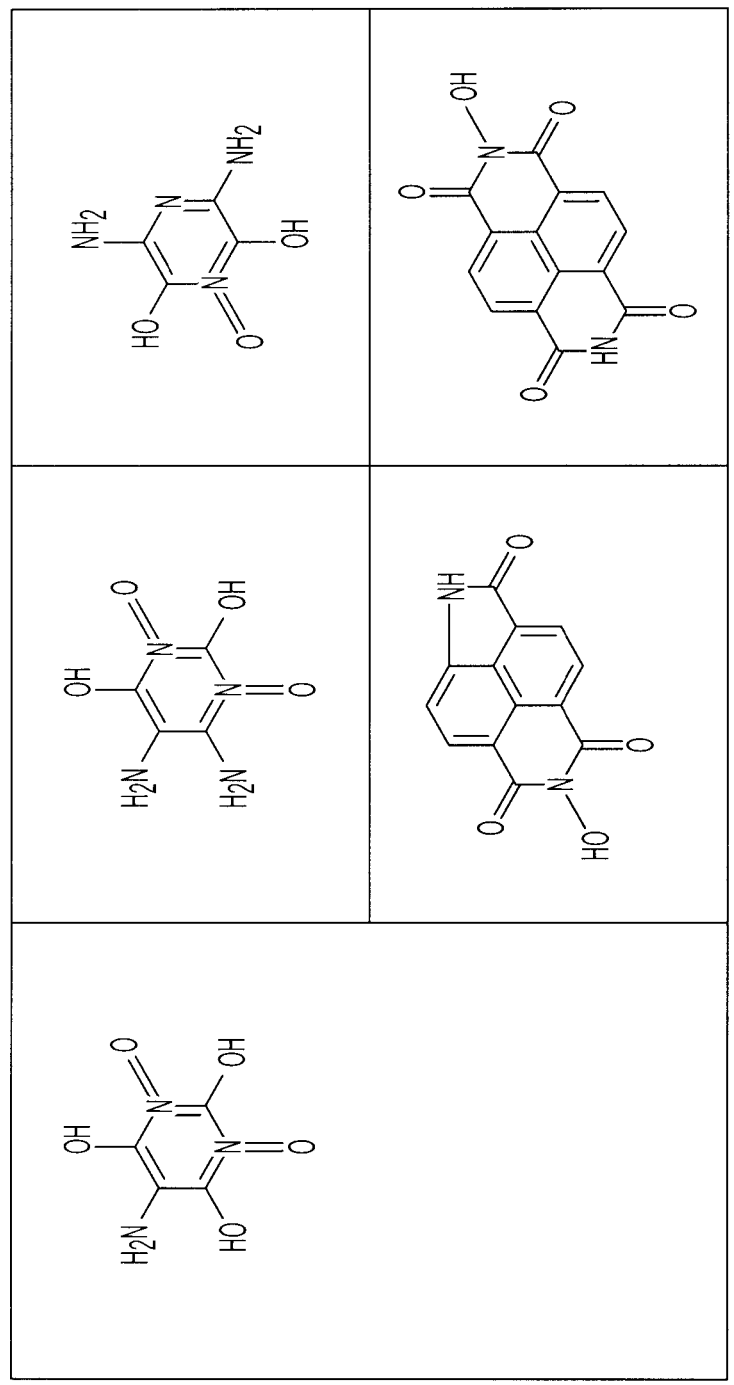
Figure 15:
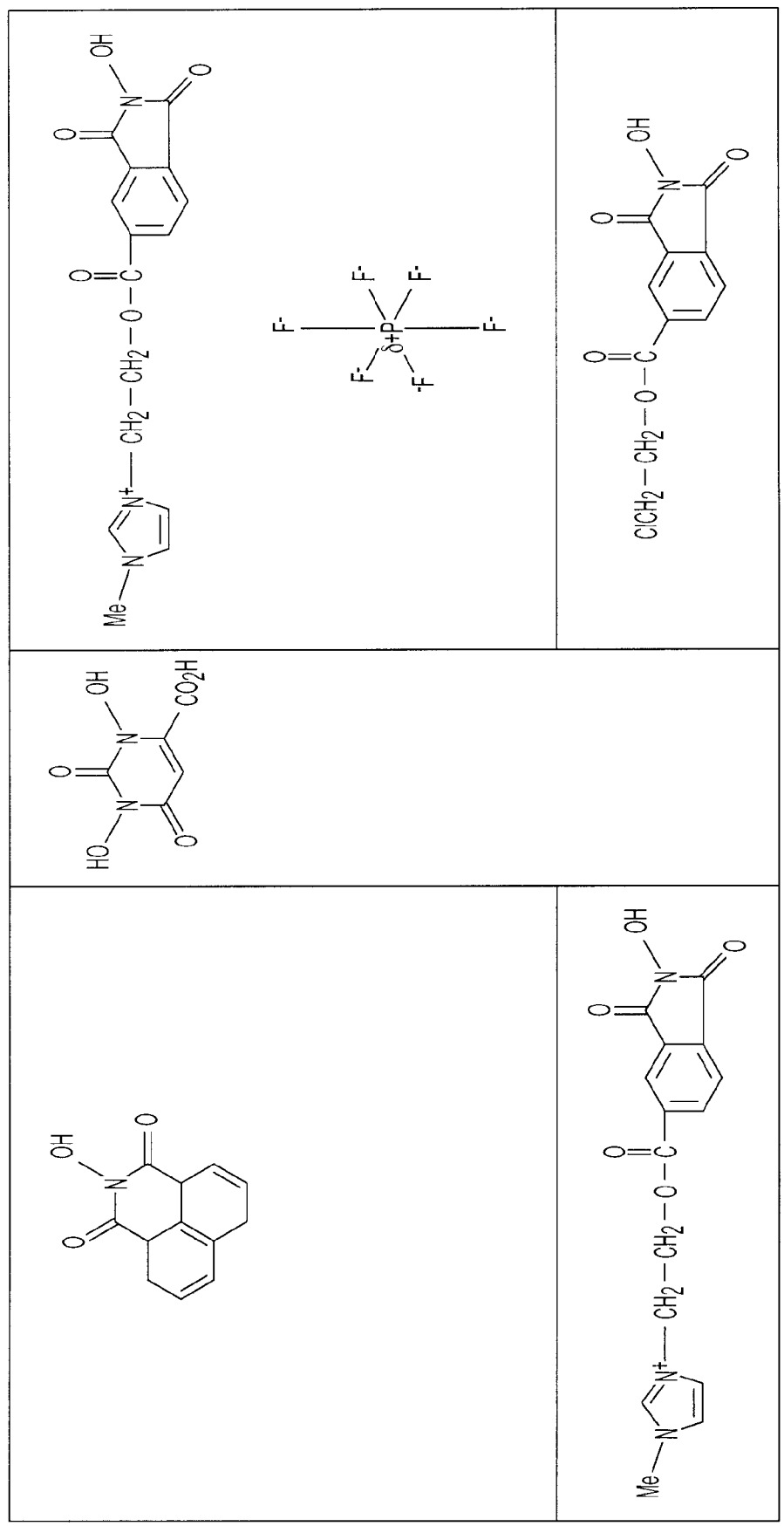
Figure 16:
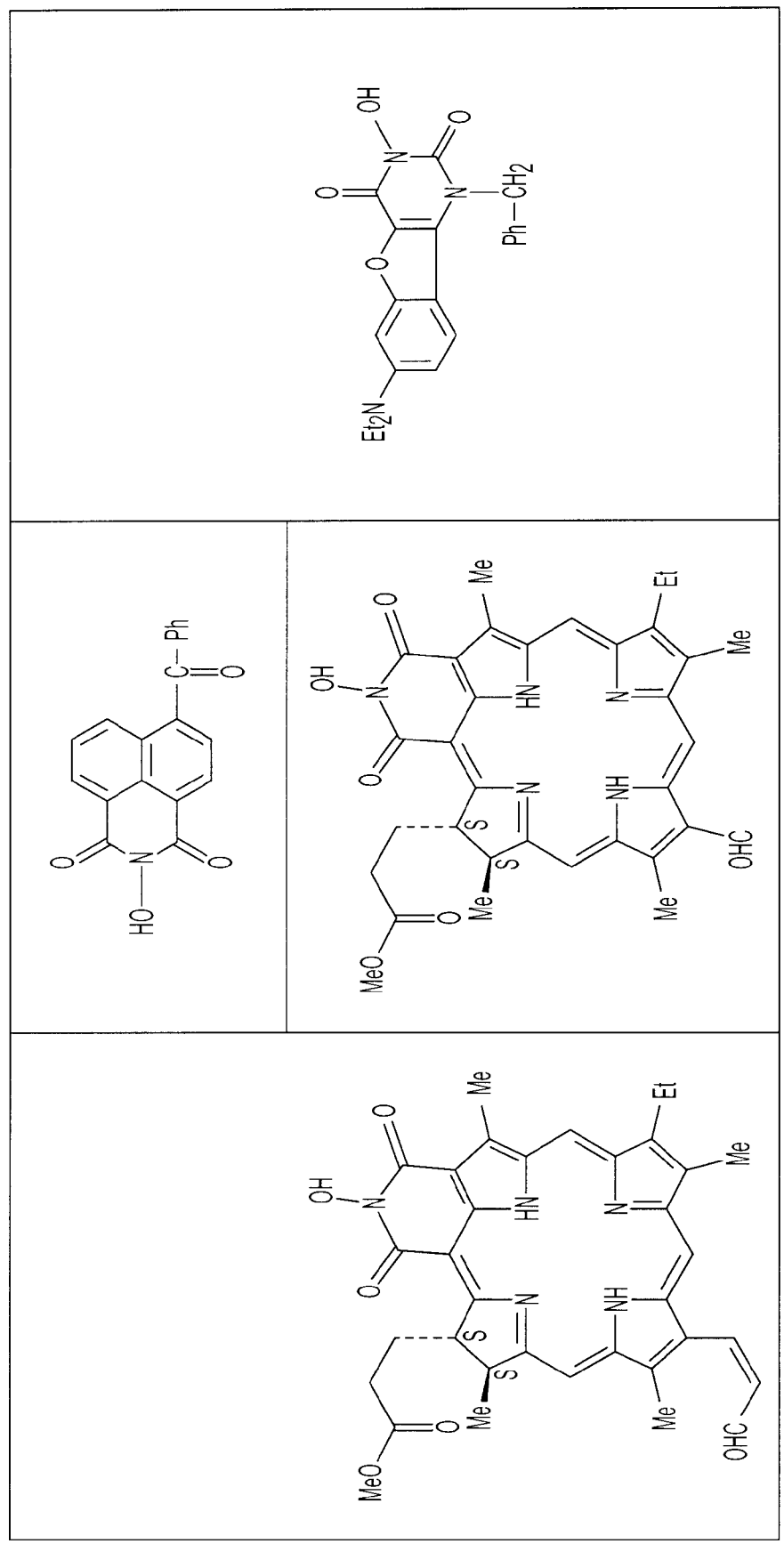
Figure 17:
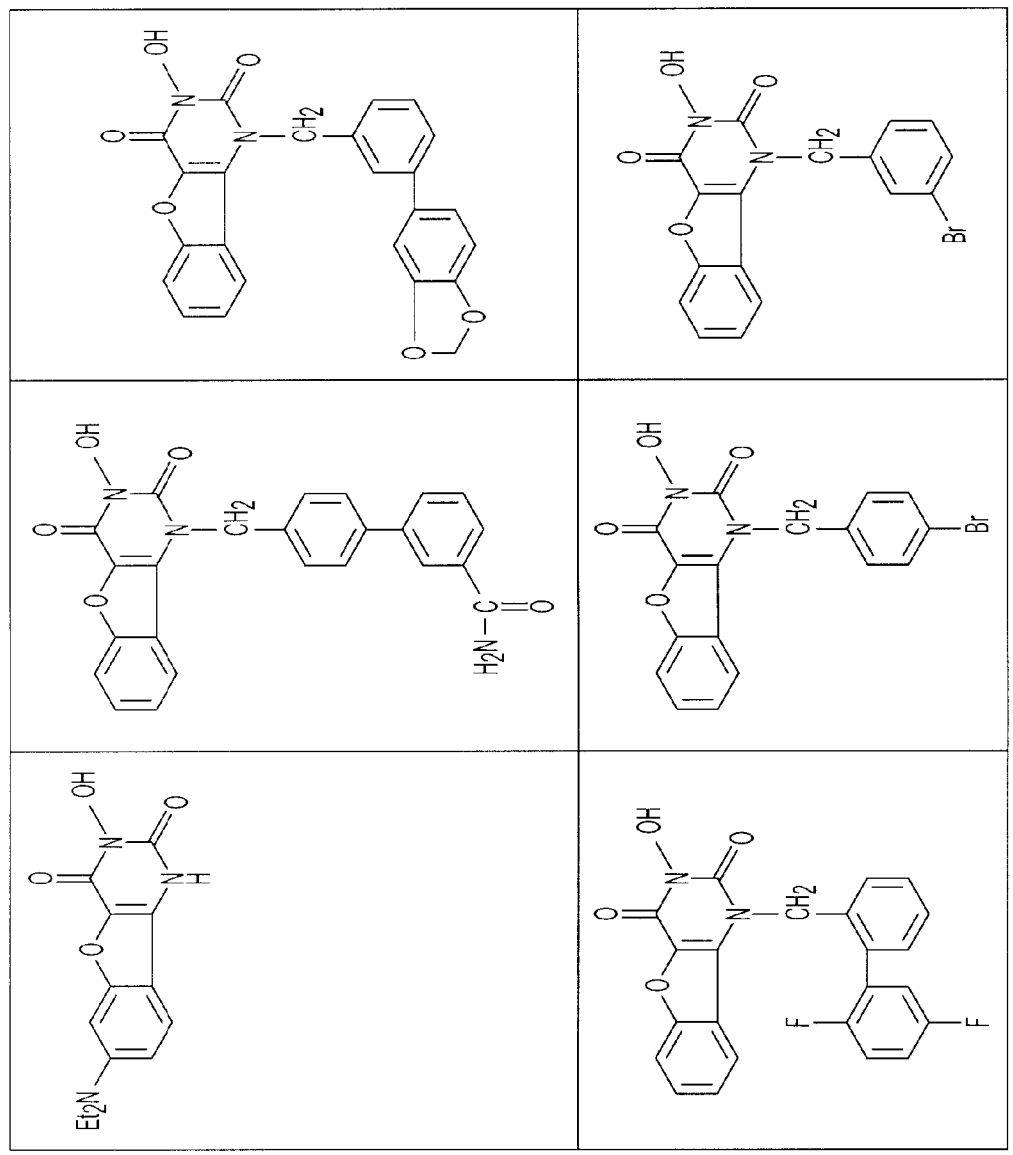
Figure 18:
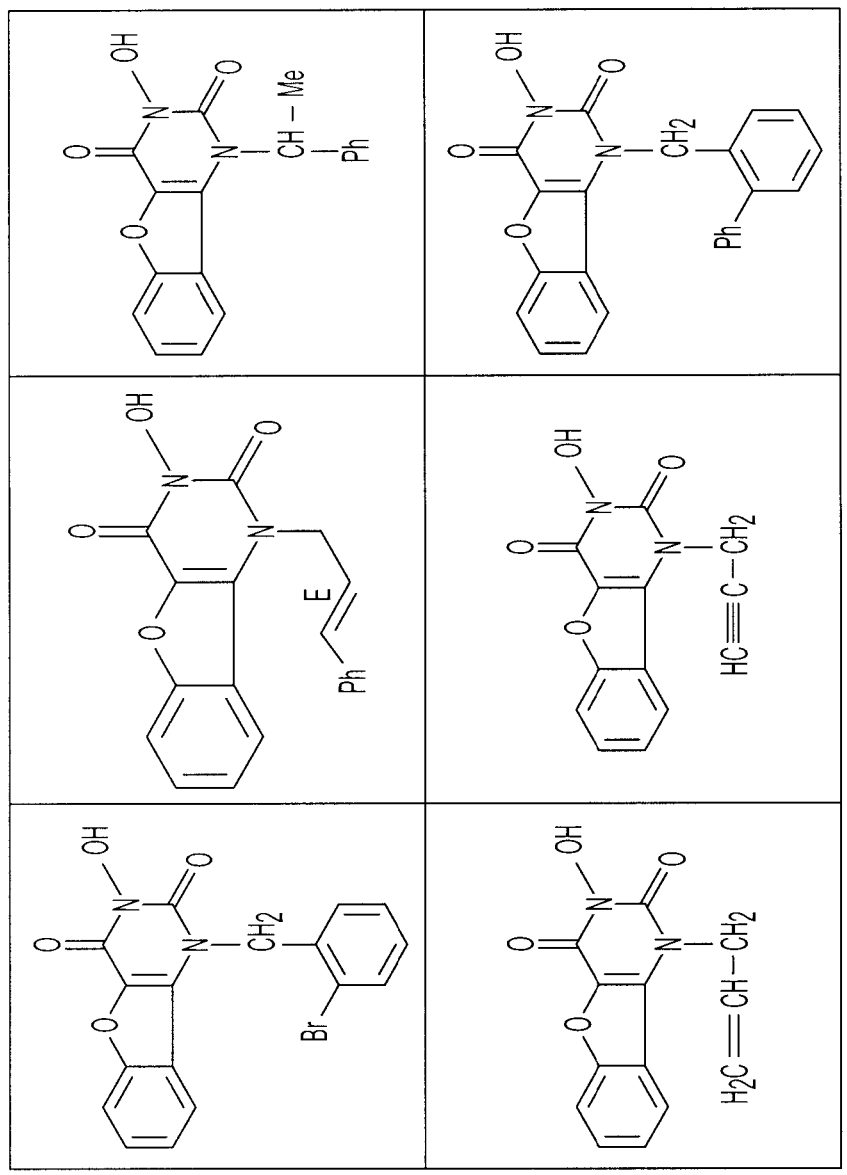
Figure 19:
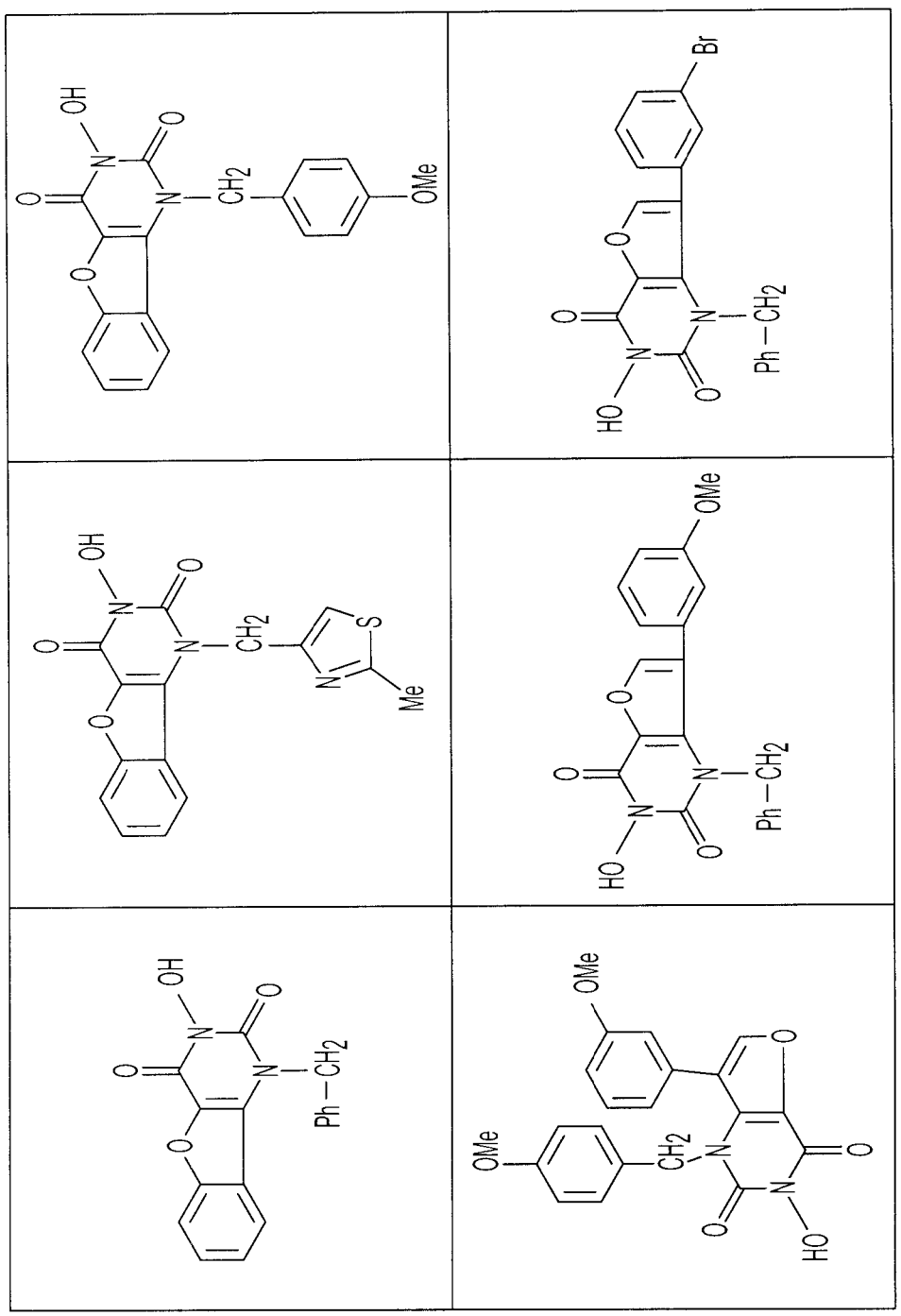
Figure 20:
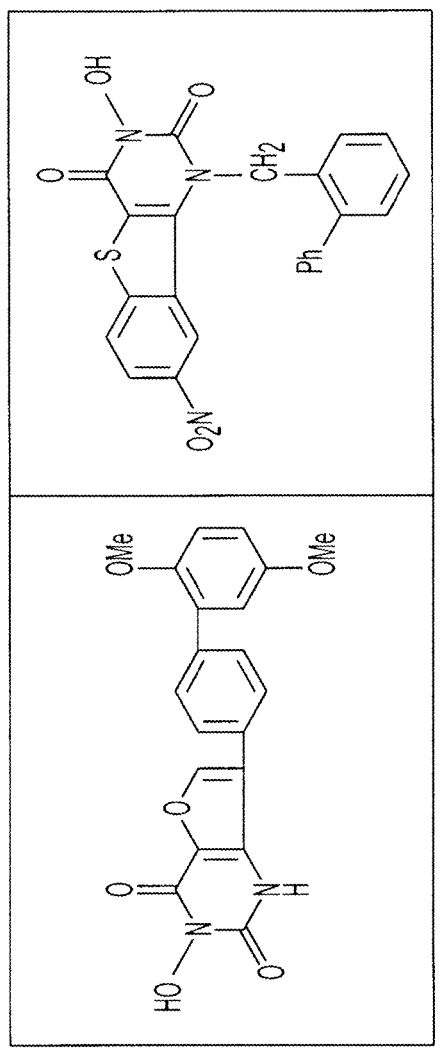

The imide of the instant invention is not limited to any one reactant as many are known in the art and are usable in the context of the instant invention, that is, to provide an intermediate derivative that does not spontaneously degrade rapidly but is stable enough to react with, for example, an amine on a desired molecule, wherein the imide, if hydroxylated and the oxygen thereof is the bonding site, is regenerated as a hydroxyimide and replaced by a functional group on the desired molecule. Examples of imides are provided in FIGS. 1-20, such as succinimide.

Cross-linked polymer matrices of the present invention may include and form hydrogels. The water content of a hydrogel may provide information on the pore structure. Further, the water content may be a factor that influences, for example, the survival of encapsulated cells within the hydrogel. The amount of water that a hydrogel is able to absorb may be related to the cross-linking density and/or pore size. For example, the percentage of imides on a functionalized macromer, such as chondroitin sulfate or keratin sulfate, may dictate the amount of water that is absorbable.

The compositions of the present invention may comprise monomers, macromers, oligomers, polymers, or a mixture thereof. The polymer compositions can consist solely of covalently crosslinkable polymers, or ionically crosslinkable polymers, or polymers crosslinkable by redox chemistry, or polymers crosslinked by hydrogen bonding, or any combination thereof. The reagents should be substantially hydrophilic and biocompatible.

Suitable hydrophilic polymers to serve as the first and second polymers include synthetic polymers such as poly (ethylene glycol), poly(ethylene oxide), partially or fully hydrolyzed poly(vinyl alcohol), poly(vinylpyrrolidone), poly (ethyloxazoline), poly(ethylene oxide)-co-poly(propylene oxide) block copolymers (poloxamers and meroxapols), poloxamines, carboxymethyl cellulose, and hydroxyalkylated celluloses such as hydroxyethyl cellulose and methylhydroxypropyl cellulose, and natural polymers such as polypeptides, polysaccharides or carbohydrates such as Ficoll™, polysucrose, hyaluronic acid, dextran, heparan sulfate, chondroitin sulfate, heparin, or alginate, and proteins such as gelatin, collagen, albumin, or ovalbumin or copolymers or blends thereof. As used herein, "celluloses" includes cellulose and derivatives of the types described above; "dextran" includes dextran and similar derivatives thereof.

Polysaccharides or other biologically compatible polymers that are very viscous liquids or that are thixotropic, and form a gel over time by the slow evolution of structure, are also useful. For example, hyaluronic acid, which can form an injectable gel with a consistency like a hair gel, may be utilized. Modified hyaluronic acid derivatives are particularly useful. As used herein, the term "modified hyaluronic acids" refers to chemically modified hyaluronic acids. Modified hyaluronic acids may be designed and synthesized with preselected chemical modifications to adjust the rate and degree of crosslinking and biodegradation. For example, modified hyaluronic acids may be designed and synthesized which are esterified with a relatively hydrophobic group such as propionic acid or benzylic acid to render the polymer more hydrophobic and gel-forming, or which are grafted with amines to promote electrostatic self-assembly. Modified hyaluronic acids thus may be synthesized which are injectable, in that they flow under stress, but maintain a gel-like structure when not under stress. Hyaluronic acid and hyaluronic derivatives are available from Genzyme, Cambridge, Mass. and Fidia, Italy.

Alternatively, a biologically compatible polymer can be incorporated into a matrix of interest to form a composite. Hence, a molecule, such as hyaluronic acid or a collagen can be incorporated into a matrix of interest. Reactivity of that incorporated biopolymer can be desired. Hence, amine groups on the introduced polymer can be reactive with the matrix components of interest, which may yield a composite structure of higher modulus. Alternatively, to gain the benefit of the polymer to the composite properties without impacting modulus substantially, such as to retain tissue adhesiveness, the introduced polymer can be functionalized to reduce activity of any reactive functions thereon. Thus, for example, the amines of a polymer, such as collagen, can be functionalized, for example, to carry an alkyl group, an acetyl group and so on as taught herein to yield a polymer less reactive with imide groups.

Methods for the synthesis of the polymers described above are known to those skilled in the art, see, for example Concise Encyclopedia of Polymer Science and Polymeric Amines and Ammonium Salts, E. Goethals, editor (Pergamen Press, Elmsford, N.Y. 1980). Many polymers, such as poly(acrylic acid), are commercially available. Naturally occurring polymers can be isolated from biological sources as known in the art or are commercially available. Naturally occurring and synthetic polymers may be modified using chemical reactions available in the art and described, for example, in March, "Advanced Organic Chemistry," 4th Edition, 1992, Wiley-Interscience Publication, New York.

Representative embodiments of the invention include a method of producing an imidated saccharide, monomer or polymer moiety, where the method can include use of a, for example, carbodiimide intermediate, and an imide reactant to form the imide-derivatized monomer. Examples of carbodiimides include N,N'-dicyclohexylcarbodiimide (DCC), N,N'-diisopropylcarbodiimide (DIC) and 1-ethyl-3-(3-dimethylaminopropyl)carbodiimide hydrochloride (EDC). Other methods for imidating a molecule are known in the art.

Numerous chemical options are available for modifying polymers that may then undergo a radical polymerization. For example, methacrylic anhydride, methacryloyl chloride and glycidyl methacrylate may be used to add methacrylate groups to one or more monomers of a polymer chain. Glycidyl methacrylate may be used, for example, for efficiency of reaction. Further, the modification reagents may be chosen to optimize a lack of cytotoxic byproducts.

In some embodiments, the number of each of the functional groups per polymeric unit may be at least one moiety per about 10 monomeric units, at least about 2 moieties per about 10 monomeric units up through one or more functional groups per monomer. Alternatively, the number of functional groups per polymeric unit may be at least one moiety per about 12 monomeric units, per about 14 monomeric units or more. For example, there may be at least about one imide group per ten monomeric units.

Moreover the ratio of each of the imide and other functional group can be 5:1, 9:2, 4:1, 7:2, 3:1, 5:2, 2:1, 3:2, 1:1, 2:3, 1:2, 2:5, 1:3, 2:7, 1:4, 2:9 or 1:5 in along the full length of the polymer. Preferably, each of the imide and other functional group is regularly distributed along the length of the polymer. However, the arrangement of the functional groups can be configured to be non-random or regular interposed, for example, to be concentrated at certain sites of the polymer backbone for an intended use. Hence, the groups can be isolated at different portions of the polymer. If aside from the imide there are two or more other functional groups, the ratio of each of the functional groups to one another can vary from unity to any other ratio or ratios as a design choice.

A composition comprising a cross-linked polymer matrix, wherein said cross-linked polymer matrix comprises at least one imidated biologically compatible polymer is provided. In some embodiments, said cross-linked polymer matrix further comprises at least two imidated biocompatible polymers. In other embodiments, a cross-linked polymer matrix further comprises a second biocompatible polymer comprising one or more functional groups reactive with the functional groups on said first imidated polymer, such as amine groups, such as, for example, found on a protein.

The accompanying molecule that can bind the imidated biopolymers of interest together, such as a polymer carrying amines, the bridging molecule, generally is a polymer that contains plural reactive sites, wherein said reactive sites are those which react with sites found on an imidated biologically compatible polymer of interest. The bridging molecule preferably is biocompatible. The bridging molecule, as with the imidated biologically compatible polymer, can be biodegradable. The bridging molecule can be configured into a multiple layered structure, wherein the internal layers can be the same or different so long as the superficial, external layers present with exposed functional group for reacting with sites on the imidated polymer which may be a tissue-adhered polymer.

Suitable polymers for the imidated polymer and bridging molecule of interest include biocompatible monomers with recurring units found in poly(phosphoesters), poly(lactides), poly(glycolides), poly(caprolactones), poly(anhydrides), poly(amides), poly(urethanes), poly(esteramides), poly(orthoesters), poly(dioxanones), poly(acetals), poly(ketals), poly(carbonates), poly(orthocarbonates), poly(phosphazenes), poly(hydroxybutyrates), poly(hydroxyl valerates), poly(alkylene oxalates), poly(alkylene succinates), poly(malic acids), poly(amino acids), polyvinylalcohol, poly(vinylpyrrolidone), poly(ethylene glycol), poly(hydroxycellulose), chitin, chitosan, and copolymers, terpolymers or combinations or mixtures of the above materials. For example, a polymer can be substituted to carry amine groups.

Other suitable synthetic polymers include polymers containing amine groups, such as chemically synthesized polypeptides. Such polypeptides may include polynucleophilic polypeptides that have been synthesized to incorporate amino acids containing primary amino groups for example, lysine, and/or amino acids containing thiol groups (such as cysteine). Further suitable synthetic polymers include poly(amino)acids.

Other compounds that may include amine groups include proteins such as albumin. Albumin may be of mammalian origin, but other sources of albumin also may be employed. Bovine serum albumin (BSA) may be used, for example. Alternatively, albumin may be recombinant albumin, isolated from cells expressing a recombinant albumin gene, using methods known in the art. Major fragments of albumin, comprising at least 100 residues of an albumin sequence, whether produced by partial proteolysis or by recombinant means, may also be used instead of intact albumin as a bridging molecule. Alternatively, useful fragments may contain at least 50 residues, and more preferably at least 75 residues of an albumin sequence. Finally, mixtures of different forms of albumin (e.g., human, bovine, recombinant, fragmented), and plasma fractions rich in albumin may also be employed. Albumin may be purified directly from tissues or cells, using methods well known in the art.

When used, polymerizing initiators include electromechanical radiation. Initiation of polymerization may be accomplished by irradiation with light at a wavelength of between about 200 to about 700 nm, or above about 320 nm or higher, or even about 365 nm.

Examples of other initiators are organic solvent-soluble initiators such as benzoyl peroxide, azobisisobutyronitrile (AIBN), di-tertiary butyl peroxide and the like, water soluble initiators such as ammonium persulfate (APS), potassium persulfate, sodium persulfate, sodium thiosulfate and the like, redox-type initiators which are combinations of such initiator and tetramethylethylene, $Fe^{2+}$ salt, sodium hydrogen sulfite or like reducing agent etc.

Useful photoinitiators are those which can be used to initiate by free radical generation polymerization of monomers with minimal cytotoxicity. In some embodiments, the initiators may work in a short time frame, for example, minutes or seconds. Exemplary dyes for UV or visible light initiation include ethyl eosin 2,2-dimethoxy-2-phenyl acetophenone, 2-methoxy-2-phenylacetophenone, other acetophenone derivatives, and camphorquinone.

Other photooxidizable and photoreducible dyes that may be used to initiate polymerization include acridine dyes, for example, acriblarine; thiazine dyes, for example, thionine; xanthine dyes, for example, rose bengal; and phenazine dyes, for example, methylene blue. These may be used with cocatalysts such as amines, for example, triethanolamine; sulphur compounds; heterocycles, for example, imidazole; enolates; organometallics; and other compounds, such as N-phenyl glycine. Other initiators include camphorquinones and acetophenone derivatives.

Thermal polymerization initiator systems may also be used. Such systems that are unstable at 37° C. and would initiate free radical polymerization at physiological temperatures include, for example, potassium persulfate, with or without tetramethyl ethylenediamine; benzoylperoxide, with or without triethanolamine; and ammonium persulfate with sodium bisulfite.

Alternatively, the first imidated polymer may react spontaneously with a surface, such as a tissue or prosthesis. The first imidated polymer also can react with the second biocompatible polymer. The two reactants can be mixed prior to application, applied simultaneously and so on as known in the art to provide polymerization of the two polymers. An initiator is used, as needed, as a design choice.

Cross-linked polymer matrices of the present invention may form and may include hydrogels. The water content of a hydrogel may provide information on the pore structure. Further, the water content may be a factor that influences, for example, the survival of encapsulated cells within the hydrogel. The amount of water that is able to be absorbed may be related to the cross-linking density pore size. For example, the percentage of methacrylate groups on a functionalized polymer may dictate the amount of water absorbable.

For example, poly(ethylene oxide)-diacrylate (PEODA) carrying an imide may be used in a polymer system for tissue engineering, and cross-linked polymer matrices may include cogels of CS-I (chondroitin sulfate-imide) and PEODA.

The mechanical properties of a cross-linked polymer matrix, such as a scaffold, may also be related to the pore structure. For applications in tissue engineering, scaffolds with different mechanical properties may be desirable depending on desired clinical application. For example, scaffolds for cartilage tissue engineering in the articular joint must survive higher mechanical stresses than a cartilage tissue engineering system in other body sites. Thus, polymers with mechanical properties that are easily manipulated may be desired, and can be obtained as a design choice.

Cytotoxicity of the biopolymer scaffold system may be evaluated with any suitable cells, such as fibroblasts, by, for example, using a live-dead fluorescent cell assay and MTT, a compound that actively metabolizing cells convert from yellow to purple, as taught hereinabove, and as known in the art.

In one aspect of this invention, a composition comprising a cross-linked polymer matrix or gel and one or more biologically active agents may be prepared. The biologically active agent may vary widely with the intended purpose for the composition. The term active is art-recognized and refers to any moiety that is a biologically, physiologically, or pharmacologically active substance that acts locally or systemically in a subject. Examples of biologically active agents, that may be referred to as "drugs", are described in well-known literature references such as the Merck Index, the Physicians Desk Reference, and The Pharmacological Basis of Therapeutics, and they include, without limitation, medicaments; vitamins; mineral supplements; substances used for the treatment, prevention, diagnosis, cure or mitigation of a disease or illness; substances which affect the structure or function of the body; or pro-drugs, which become biologically active or more active after they have been placed in a physiological environment. Various forms of a biologically active agent may be used which are capable of being released the subject composition, for example, into adjacent tissues or fluids upon administration to a subject. In some embodiments, a biologically active agent may be used in cross-linked polymer matrix of this invention, to, for example, promote cartilage formation. In other embodiments, a biologically active agent may be used in cross-linked polymer matrix of this invention, to treat, ameliorate, inhibit, or prevent a disease or symptom, in conjunction with, for example, promoting cartilage formation.

Further examples of biologically active agents include, without limitation, enzymes, receptor antagonists or agonists, hormones, growth factors, autogenous bone marrow, antibiotics, antimicrobial agents and antibodies. The term "biologically active agent" is also intended to encompass various cell types and genes that can be incorporated into the compositions of the invention.

In certain embodiments, the subject compositions comprise about 1% to about 75% or more by weight of the total composition, alternatively about 2.5%, 5%, 10%, 20%, 30%, 40%, 50%, 60% or 70%, of a biologically active agent.

Non-limiting examples of biologically active agents include following: adrenergic blocking agents, anabolic agents, androgenic steroids, antacids, anti-asthmatic agents, anti-allergenic materials, anti-cholesterolemic and anti-lipid agents, anti-cholinergics and sympathomimetics, anti-coagulants, anti-convulsants, anti-diarrheal~, anti-emetics, anti-hypertensive agents, anti-infective agents, anti-inflammatory agents such as steroids, non-steroidal anti-inflammatory agents, anti-malarials, anti-manic agents, anti-nauseants, anti-neoplastic agents, anti-obesity agents, anti-parkinsonian agents, anti-pyretic and analgesic agents, anti-spasmodic agents, anti-thrombotic agents, anti-uricemic agents, anti-anginal agents, antihistamines, anti-tussives, appetite suppressants, benzophenanthridine alkaloids, biologicals, cardioactive agents, cerebral dilators, coronary dilators, decongestants, diuretics, diagnostic agents, erythropoietic agents, estrogens, expectorants, gastrointestinal sedatives, agents, hyperglycemic agents, hypnotics, hypoglycemic agents, ion exchange resins, laxatives, mineral supplements, mitotics, mucolytic agents, growth factors, neuromuscular drugs, nutritional substances, peripheral vasodilators, progestational agents, prostaglandins, psychic energizers, psychotropics, sedatives, stimulants, thyroid and anti-thyroid agents, tranquilizers, uterine relaxants, vitamins, antigenic materials, and prodrugs.

Specific examples of useful biologically active agents the above categories include: (a) anti-neoplastics such as androgen inhibitors, antimetabolites, cytotoxic agents, and immunomodulators; (b) anti-tussives such as dextromethorphan, hydrobromide, noscapine, carbetapentane citrate, and chlophedianol hydrochloride; (c) antihistamines such as chlorpheniramine phenindamine tartrate, pyrilamine doxylamine succinate, and phenyltoloxamine citrate; (d) decongestants such as hydrochloride, phenylpropanolamine hydrochloride, pseudoephedrine hydrochloride, and ephedrine; (e) various alkaloids such as codeine phosphate, codeine sulfate, and morphine; (f) mineral supplements such as potassium chloride, zinc chloride, calcium carbonate, magnesium oxide, and other alkali metal and alkaline earth metal salts; (g) ion exchange resins such as such as N-acetylprocainamide; (i) antipyretics and analgesics such as acetaminophen, aspirin and ibuprofen; appetite suppressants such as phenyl-propanolamine or caffeine; (k) expectorants such as guaifenesin; (l) antacids such as aluminum hydroxide and magnesium hydroxide; biologicals such as peptides, polypeptides, proteins and amino acids, hormones, interferons or cytokines and other bioactive peptidic compounds, such as calcitonin, ANF, EPO and insulin; (n) anti-infective agents such as anti-fungals, anti-virals, antiseptics and antibiotics; and (m) desensitizing agents and antigenic materials, such as those useful for vaccine applications.

More specifically, non-limiting examples of useful biologically active agents include the following therapeutic categories: analgesics, such as nonsteroidal anti-inflammatory drugs, opiate agonists and salicylates; antihistamines, such as H1-blockers and H2-blockers; anti-infective agents, such as antihelmintics, antianaerobics, antibiotics, aminoglycoside antibiotics, antifungal antibiotics, cephalosporin antibiotics, macrolide antibiotics, miscellaneous antibiotics, penicillin antibiotics, quinolone antibiotics, sulfonamide antibiotics, tetracycline antibiotics, antimycobacterials, antituberculosis antimycobacterials, antiprotozoals, antimalarial antiprotozoals, antiviral agents, anti-retroviral agents, scabicides, and urinary anti-infectives; antineoplastic agents, such as alkylating agents, nitrogen mustard alkylating agents, nitrosourea alkylating agents, antimetabolites, purine analog antimetabolites, pyrimidine analog antimetabolites, hormonal antineoplastics, natural antineoplastics, antibiotic natural antineoplastics, and vinca alkaloid natural antineoplastics; autonomic agents, such as anticholinergics, antimuscarinic anticholinergics, ergot alkaloids, parasympathomimetics, cholinergic agonist parasympathomimetics, cholinesterase inhibitor parasympathomimetics, sympatholytics, α-blocker sympatholytics, sympatholytics, sympathomimetics, and adrenergic agonist sympathomimetics; cardiovascular agents, such as antianginals, antianginals, calcium-channel blocker antianginals, nitrate antianginals, antiarrhythmics, cardiac glycoside antiarrhythmics, class I antiarrhythmics, class antiarrhythmics, class antiarrhythmics, class IV antiarrhythmics, antihypertensive agents, α-blocker antihypertensives, angiotensin-converting enzyme inhibitor (ACE inhibitor) antihypertensives, 13-blocker antihypertensives, calcium-channel blocker antihypertensives, central-acting adrenergic antihypertensives, diuretic antihypertensive agents, peripheral vasodilator antihypertensives, antilipemics, bile acid sequestrant antilipemics, reductase inhibitor antilipemics, inotropes, cardiac glycoside inotropes, and thrombolytic agents; dermatological agents, such as antihistamines, anti-inflammatory agents, corticosteroid anti-inflammatory agents, anesthetics, topical anti-infectives, topical anti-infectives, antiviral topical anti-infectives, and topical antineoplastics; electrolytic and renal agents, such as acidifying agents, alkalinizing agents, diuretics, carbonic anhydrase inhibitor diuretics, loop diuretics, osmotic diuretics, potassium-sparing diuretics, thiazide diuretics, electrolyte replacements, and uricosuric agents; enzymes, such as pancreatic enzymes and thrombolytic enzymes; gastrointestinal agents, such as antidiarrheals, antiemetics, gastrointestinal anti-inflammatory agents, salicylate gastrointestinal anti-inflammatory agents, antacid anti-ulcer agents, gastric acid-pump inhibitor anti-ulcer agents, gastric mucosal anti-ulcer agents, H2-blocker anti-ulcer agents, cholelitholytic agents, digestants, emetics, laxatives and stool softeners, and prokinetic agents; general anesthetics, such as inhalation anesthetics, halogenated inhalation anesthetics, intravenous anesthetics, barbiturate intravenous anesthetics, benzodiazepine intravenous anesthetics, and opiate agonist intravenous anesthetics; hematological agents, such as antianemia agents, hematopoietic antianemia agents, coagulation agents, anticoagulants, hemostatic coagulation agents, platelet inhibitor coagulation agents, thrombolytic enzyme coagulation agents, and plasma volume expanders; hormones and hormone modifiers, such as abortifacients, adrenal agents, corticosteroid adrenal agents, androgens, anti-androgens, antidiabetic agents, sulfonylurea antidiabetic agents, antihypoglycemic agents, oral contraceptives, progestin contraceptives, estrogens, fertility agents, oxytocics, parathyroid agents, pituitary hormones, progestins, antithyroid agents, thyroid hormones, and tocolytics; immunobiologic agents, such as immunoglobulins, immunosuppressives, toxoids, and vaccines; local anesthetics, such as amide local anesthetics and ester local anesthetics; musculoskeletal agents, such as anti-gout anti-inflammatory agents, corticosteroid anti-inflammatory agents, gold compound anti-inflammatory agents, immunosuppressive anti-inflammatory agents, nonsteroidal anti-inflammatory drugs, salicylate anti-inflammatory agents, skeletal muscle relaxants, neuromuscular blocker skeletal muscle relaxants, and reverse neuromuscular blocker skeletal muscle relaxants; neurological agents, such as anticonvulsants, barbiturate anticonvulsants, benzodiazepine anticonvulsants, anti-migraine agents, anti-parkinsonian agents, anti-vertigo agents, opiate agonists, and opiate antagonists; ophthalmic agents, such as anti-glaucoma agents, anti-glaucoma agents, mitotics, anti-glaucoma agents, mydriatics, adrenergic agonist mydriatics, antimuscarinic mydriatics, ophthalmic anesthetics, ophthalmic anti-infectives, ophthalmic aminoglycoside anti-infectives, ophthalmic macrolide anti-infectives, ophthalmic quinolone anti-infectives, ophthalmic sulfonamide anti-infectives, ophthalmic tetracycline anti-infectives, ophthalmic anti-inflammatory agents, ophthalmic corticosteroid anti-inflammatory agents, and ophthalmic nonsteroidal anti-inflammatory drugs; psychotropic agents, such as antidepressants, heterocyclic antidepressants, monoamine oxidase inhibitors selective serotonin re-uptake inhibitors tricyclic antidepressants, antimanics, antipsychotics, phenothiazine antipsychotics, anxiolytics, sedatives, and hypnotics, barbiturate sedatives and hypnotics, benzodiazepine anxiolytics, sedatives, and hypnotics, and psychostimulants; respiratory agents, such as antitussives, bronchodilators, adrenergic agonist bronchodilators, antimuscarinic bronchodilators, expectorants, mucolytic agents, respiratory anti-inflammatory agents, and respiratory corticosteroid anti-inflammatory agents; toxicology agents, such as antidotes, heavy agents, substance abuse agents, deterrent substance abuse agents, and withdrawal substance abuse agents; minerals; and vitamins, such as vitamin A, vitamin vitamin C, vitamin D, vitamin E, and vitamin K.

Other classes of biologically active agents from the above categories include: (1) analgesics in general, such as lidocaine, other "caine" analgesics or derivatives thereof, and nonsteroidal anti-inflammatory drugs (NSAIDs) analgesics, including diclofenac, ibuprofen, ketoprofen, and naproxen; (2) opiate agonist analgesics, such as codeine, fentanyl, hydromorphone, and morphine; (3) salicylate analgesics, such as aspirin (ASA) (enteric coated ASA); (4) H1-blocker antihistamines, such as clemastine and terfenadine; (5) H2-blocker antihistamines, such as cimetidine, famotidine, nizadine, and ranitidine; (6) anti-infective agents, such as mupirocin; (7) antianaerobic anti-infectives, such as chloramphenicol and clindarnycin; (8) antifungal antibiotic anti-infectives, such as amphotericin b, clotrimazole, fluconazole, and ketoconazole; (9) macrolide antibiotic anti-infectives, such as azithromycin and erythromycin; (10) miscellaneous antibiotic anti-infectives, such as and imipenem; penicillin antibiotic anti-infectives, such as nafcillin, oxacillin, penicillin G, and penicillin V; (12) quinolone antibiotic anti-infectives, such as ciprofloxacin and norfloxacin; (13) tetracycline antibiotic anti-infectives, such as doxycycline, minocycline and tetracycline; (14) antituberculosis antimycobacterial anti-infectives such as isoniazid and rifampin; (15) antiprotozoal anti-infectives, such as atovaquone and dapsone; (16) antimalarial antiprotozoal anti-infectives, such as chloroquine and pyrimethamine; (17) anti-retroviral anti-infectives, such as ritonavir and zidovudine; (18) antiviral anti-infective agents, such as acyclovir, ganciclovir, interferon-α, and rimantadine; (19) alkylating antineoplastic agents, such as carboplatin and cisplatin; (20) nitrosourea alkylating antineoplastic agents, such as carmustine (BCNU); (21) antimetabolite antineoplastic agents, such as methotrexate; (22) pyrimidine analog antineoplastic agents, such as fluorouracil (5-FU) and gemcitabine; (23) hormonal antineoplastics, such as goserelin, leuprolide, and tamoxifen; (24) natural antineoplastics, such as aldesleukin, interleukin-2, docetaxel, etoposide interferon α, paclitaxel, other taxane derivatives, and tretinoin (ATRA); (25) antibiotic natural antineoplastics, such as bleomycin, dactinomycin, daunorubicin, doxorubicin, and mitomycin; (26) vinca alkaloid natural antineoplastics, such as vinblastine and vincristine; (27) autonomic agents, such as nicotine; (28) anticholinergic autonomic agents, such as benztropine and trihexyphenidyl; (29) antimuscarinic anticholinergic autonomic agents, such as atropine and oxybutynin; (30) ergot alkaloid autonomic agents, such as bromocriptine; (31) cholinergic agonist parasympathomimetics, such as pilocarpine; (32) cholinesterase inhibitor parasympathomimetics, such as pyridostigmine; (33) a-blocker sympatholytics, such as prazosin; (34) D-blocker sympatholytics, such as atenolol; (35) adrenergic sympathomimetics, such as albuterol and dobutamine; (36) cardiovascular agents, such as aspirin (ASA) (enteric coated ASA); (37) D-blocker antianginals, such as atenolol and propranolol; (38) calcium-channel blocker antianginals, such as nifedipine and verapamil; (39) nitrate antianginals, such as isosorbide dinitrate (ISDN); (40) cardiac glycoside antiarrhythmics, such as (41) class I antiarrhythmics, such as lidocaine, mexiletine, phenyloin, procainamide, and quinidine; (42) class antiarrhythmics, such as atenolol, metoprolol, propranolol, and timolol; (43) class antiarrhythmics, such as amiodarone; (44) class IV antiarrhythmics, such as diltiazem and verapamil; (45) antihypertensives, such as prazosin; (46) angiotensin-converting enzyme inhibitor (ACE inhibitor) antihypertensives, such as captopril and enalapril; (47) antihypertensives, such as atenolol, metoprolol, nadolol, and propanolol; (48) calcium-channel blocker antihypertensive agents, such as diltiazem and nifedipine; (49) central-acting adrenergic antihypertensives, such as clonidine and methyldopa; (50) diuretic antihypertensive agents, such as amiloride, furosemide, hydrochlorothiazide (HCTZ), and spironolactone; (51) peripheral vasodilator antihypertensives, such as and minoxidil; (52) antilipemics, such as gemfibrozil and probucol; (53) bile acid sequestrant antilipemics, such as cholestyramine; (54) reductase inhibitor antilipemics, such as lovastatin and pravastatin; (55) inotropes, such as aminone, dobutamine, and dopamine; (56) cardiac glycoside inotropes, such as (57) thrombolytic agents, such as alteplase (TPA), anistreplase, streptokinase, and urokinase; (58) dermatological agents, such as colchicine, isotretinoin, methotrexate, minoxidil, tretinoin (59) dermatological corticosteroid anti-inflammatory agents, such as betamethasone and dexamethasone; (60) antifungal topical anti-infectives, such as amphotericin clotrimazole, miconazole, and nystatin; (61) antiviral topical anti-infectives, such as acyclovir; (62) topical antineoplastics, such as (63) electrolytic and renal agents, such as lactulose; (64) loop diuretics, such as furosemide; (65) potassium-sparing diuretics, such as triamterene; (66) thiazide diuretics, such as hydrochlorothiazide (HCTZ); (67) uricosuric agents, such as probenecid; (68) enzymes such as and (69) thrombolytic enzymes, such as alteplase, anistreplase, streptokinase and urokinase; (70) antiemetics, such as prochlorperazine; (71) salicylate gastrointestinal anti-inflammatory agents, such as sulfasalazine; (72) gastric acid-pump inhibitor anti-ulcer agents, such as omeprazole; (73) H2-blocker anti-ulcer agents, such as cimetidine, famotidine, nizatidine, ranitidine; (74) digestants, such as pancrelipase; (75) prokinetic agents, such as erythromycin; (76) opiate agonist intravenous anesthetics such as fentanyl; (77) hematopoietic antianemia agents, such as (G-CSF), and (GM-CSF); (78) coagulation agents, such as factors 1-10 (AHF 1-10); (79) anticoagulants, such as warfarin; (80) thrombolytic enzyme coagulation agents, such as alteplase, anistreplase, streptokinase and urokinase; (81) hormones and hormone modifiers, such as bromocriptine; (82) abortifacients, such as methotrexate; (83) antidiabetic agents, such as insulin; (84) oral contraceptives, such as estrogen and progestin; (85) progestin contraceptives, such as levonorgestrel and norgestrel; (86) estrogens such as conjugated estrogens, diethylstilbestrol (DES), estrogen (estradiol, estrone, and estropipate); (87) fertility agents, such as clomiphene, human chorionic gonadotropin (HCG), and menotropins; (88) parathyroid agents such as calcitonin; (89) pituitary hormones, such as desmopressin, goserelin, oxytocin, and vasopressin (ADH); (90) progestins, such as medroxyprogesterone, norethindrone, and progesterone; (91) thyroid hormones, such as levothyroxine; (92) immunobiologic agents, such as interferon beta-1b and interferon gamma-1b; (93) immunoglobulins, such as immune globulin IM, IMIG, IGIM and immune globulin IVIG, IGIV; (94) amide local anesthetics, as lidocaine; (95) ester local anesthetics, such as benzocaine and procaine; (96) musculoskeletal corticosteroid anti-inflammatory agents, such as beclomethasone, betamethasone, cortisone, dexamethasone, hydrocortisone, and prednisone; (97) musculoskeletal anti-inflammatory immunosuppressives, such as azathioprine, cyclophosphamide, and methotrexate; (98) musculoskeletal nonsteroidal anti-inflammatory drugs such as diclofenac, ibuprofen, ketoprofen, ketorlac, and naproxen; (99) skeletal muscle relaxants, such as and diazepam; (100) reverse neuromuscular blocker skeletal muscle relaxants, such as pyridostigmine; (101) neurological agents, such as nimodipine, riluzole, tacrine and ticlopidine; (102) anticonvulsants, such as carbamazepine, gabapentin, lamotrigine, phenyloin, and valproic acid; (103) barbiturate anticonvulsants, such as phenobarbital and primidone; (104) benzodiazepine anticonvulsants, such as clonazepam, diazepam, and lorazepam; (105) anti-agents, such as bromocriptine, levodopa, carbidopa, and pergolide; (106) anti-vertigo agents, such as meclizine; (107) opiate agonists, such as codeine, fentanyl, hydromorphone, methadone, and morphine; (108) opiate antagonists, such as naloxone; (109) antiglaucoma agents, such as timolol; (110) mitotic anti-glaucoma agents, such as pilocarpine; (111) ophthalmic aminoglycoside anti-infectives, such as gentamicin, neomycin, and tobramycin; (112) ophthalmic quinolone anti-infectives, such as ciprofloxacin, norfloxacin, and ofloxacin; (113) ophthalmic corticosteroid anti-agents, such as dexamethasone and prednisolone; (114) ophthalmic nonsteroidal anti-inflammatory drugs such as diclofenac; (115) antipsychotics, such as clozapine, haloperidol, and risperidone; (116) benzodiazepine anxiolytics, sedatives and hypnotics, such as clonazepam, diazepam, lorazepam, oxazepam, and prazepam; (117) psychostimulants, such as methylphenidate and pemoline; (118) such as codeine; (119) bronchodilators, such as (120) adrenergic agonist bronchodilators, such as albuterol; (121) respiratory corticosteroid anti-inflammatory agents, such as dexamethasone; (122) antidotes, such as flumazenil and naloxone; (123) heavy metal agents, such as penicillamine; (124) deterrent substance abuse agents, such as disulfuram, naltrexone, and nicotine; (125) withdrawal substance abuse agents, such as bromocriptine; (126) minerals, such as iron, calcium, and magnesium; (127) vitamin B compounds, such as cyanocobalamin (vitamin B12) and niacin (vitamin B3); (128) vitamin C compounds, such as ascorbic acid; and (129) vitamin D such as calcitriol.

Further, recombinant or cell-derived proteins may be used, such as: recombinant beta-glucan; bovine immunoglobulin concentrate; bovine superoxide dismutase; formulation comprising fluorouracil, epinephrine, and bovine collagen; recombinant hirudin (r-Hir), HIV-1 immunogen; recombinant human growth hormone recombinant EPO (r-EPO); gene-activated EPO (GA-EPO); recombinant human hemoglobin (r-Hb); recombinant human mecasermin (r-IGF-1); recombinant interferon β; lenograstim (G-CSF); olanzapine; recombinant thyroid stimulating hormone (r-TSH); and topotecan.

Still further, the following listing of peptides, proteins, and other large molecules may also be used, such as interleukins 1 through 18, including mutants and analogues; interferons a, y, and which may be useful for cartilage regeneration, hormone releasing hormone (LHRH) and analogues, gonadotropin releasing hormone transforming growth factor (TGF); fibroblast growth factor (FGF); tumor necrosis factor-a y and y); nerve growth factor (NGF); growth hormone releasing factor (GHRF), epidermal growth factor (EGF), connective tissue activated osteogenic factors, fibroblast growth factor homologous factor (FGFHF); hepatocyte growth factor (HGF); insulin growth factor (IGF); invasion inhibiting factor-2 (IIF-2); bone morphogenetic proteins 1-7 (BMP 1-7); somatostatin; thymosin-a-y-globulin; superoxide dismutase (SOD); and complement factors, and biologically active analogs, fragments, and derivatives of such factors, for example, growth factors.

Members of the transforming growth factor (TGF) supergene family, which are multifunctional regulatory proteins, may be incorporated in a polymer matrix of the present invention. Members of the TGF supergene family include the beta transforming growth factors (for example, TGF-β1, TGF-β2, TGF-β3); bone morphogenetic proteins (for example, BMP-1, BMP-2, BMP-3, BMP-4, BMP-5, BMP-6, BMP-7, BMP-8, BMP-9); heparin-binding growth factors (for example, fibroblast growth factor (FGF), epidermal growth factor (EGF), platelet-derived growth factor (PDGF), insulin-like growth factor (IGF)), (for example, Inhibin A, Inhibin B), growth differentiating factors (for example, GDF-1); and Activins (for example, Activin A, Activin B, Activin AB). Growth factors can be isolated from native or natural sources, such as from mammalian cells, or can be prepared synthetically, such as by recombinant DNA techniques or by various chemical processes. In addition, analogs, fragments, or derivatives of these factors can be used, provided that they exhibit at least some of the biological activity of the native molecule. For example, analogs can be prepared by expression of genes altered by site-specific mutagenesis or other genetic engineering techniques.

Various forms of the biologically active agents may be used. These include, without limitation, such forms as uncharged molecules, molecular complexes, salts, ethers, esters, amides, prodrug forms and the like, which are biologically activated when implanted, injected or otherwise placed into a subject.

In certain embodiments, other materials may be incorporated into subject compositions in addition to one or more biologically active agents. For example, plasticizers and stabilizing agents known in the art may be incorporated in compositions of the present invention. In certain embodiments, additives such as plasticizers and stabilizing agents are selected for their biocompatibility or for the resulting physical properties of the reagents, the setting or gelling matrix or the set or gelled matrix.

A composition of this invention may further contain one or more adjuvant substances or the like. Such additional materials may affect the characteristics of the resulting composition. For example, fillers, such as bovine serum albumin (BSA) or mouse serum albumin (MSA), may be associated with the polymer composition. In certain embodiments, the amount of filler may range from about 0.1 to about 50% or more by weight of the composition. Incorporation of such fillers may affect the sustained release rate of any encapsulated substance. Other fillers known to those of skill in the art, such as carbohydrates, sugars, starches, saccharides, celluloses and polysaccharides, including and sucrose, may be used in certain embodiments in the present invention.

Buffers, acids and bases may be incorporated in the compositions to adjust pH. Agents to increase the diffusion distance of agents released from the composition may also be included.

The charge, lipophilicity or hydrophilicity of a subject composition may be modified by employing an additive. For example, surfactants may be used to enhance miscibility of poorly miscible liquids. Examples of suitable surfactants include dextran, polysorbates and sodium lauryl sulfate. In general, surfactants are used in low concentrations, generally less than about 5%.

The specific method used to formulate the novel formulations described herein is not critical to the present invention and can be selected from a physiological buffer (Feigner et al., U.S. Pat. No. 5,589,466 (1996)).

Therapeutic formulations of the product may be prepared for storage as lyophilized formulations or aqueous solutions by mixing the product having the desired degree of purity with optional pharmaceutically acceptable carriers, diluents, excipients or stabilizers typically employed in the art, i.e., buffering agents, stabilizing agents, preservatives, isotonifiers, non-ionic detergents, antioxidants and other miscellaneous additives, see Remington's Pharmaceutical Sciences, 16th ed., Osol, ed. (1980). Such additives are generally non-toxic to the recipients at the dosages and concentrations employed, hence, the excipients, diluents, carriers and so on are pharmaceutically acceptable.

An "isolated" or "purified" polymer of interest is substantially free of contaminating proteins from the medium or tissue source from which the polymer is obtained, or substantially free of chemical precursors or other chemicals or reactants in the medium or reaction mixture used which contains components that are chemically synthesized. Thus, an isolated or purified imidated polymer is substantially free of non-imidated polymer material and includes preparations of less than about 30%, 20%, 25%, 20%, 10%, 5%, 4%, 3%, 2.5%, 2%, 1.5% or 1% or less, (by dry weight) of non-imidated biopolymer contaminants.

As used herein, the terms "stability" and "stable" in the context of a liquid formulation comprising a biopolymer of interest that is resistant to thermal and chemical aggregation, degradation or fragmentation under given manufacture, preparation, transportation and storage conditions, such as, for one month, for two months, for three months, for four months, for five months, for six months or more. The "stable" formulations of the invention retain biological activity equal to or more than 80%, 85%, 90%, 95%, 98%, 99% or 99.5% under given manufacture, preparation, transportation and storage conditions. The stability of said preparation can be assessed by degrees of aggregation, degradation or fragmentation by methods known to those skilled in the art.

The term, "carrier," refers to a diluent, adjuvant, excipient or vehicle with which the therapeutic is administered. Such physiological carriers can be sterile liquids, such as water and oils, including those of petroleum, animal, vegetable or synthetic origin, such as peanut oil, soybean oil, mineral oil, sesame oil and the like. Water is a suitable carrier when the pharmaceutical composition is administered intravenously. Saline solutions and aqueous dextrose and glycerol solutions also can be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol and the like. The composition, if desired, can also contain minor amounts of wetting or emulsifying agents, or pH buffering agents.

The compositions can take the form of solutions, suspensions, emulsions, powders, sustained-release formulations, depots and the like. Examples of suitable carriers are described in "Remington's Pharmaceutical Sciences," Martin. Such compositions will contain an effective amount of the biopolymer of interest, preferably in purified form, together with a suitable amount of carrier so as to provide the form for proper administration to the patient. As known in the art, the formulation will be constructed to suit the mode of administration.

Buffering agents help to maintain the pH in the range which approximates physiological conditions. Buffers are preferably present at a concentration ranging from about 2 mM to about 50 mM. Suitable buffering agents for use with the instant invention include both organic and inorganic acids, and salts thereof, such as citrate buffers (e.g., monosodium citrate-disodium citrate mixture, citric acid-trisodium citrate mixture, citric acid-monosodium citrate mixture etc.), succinate buffers (e.g., succinic acid-monosodium succinate mixture, succinic acid-sodium hydroxide mixture, succinic acid-disodium succinate mixture etc.), tartrate buffers (e.g., tartaric acid-sodium tartrate mixture, tartaric acid-potassium tartrate mixture, tartaric acid-sodium hydroxide mixture etc.), fumarate buffers (e.g., fumaric acid-monosodium fumarate mixture, fumaric acid-disodium fumarate mixture, monosodium fumarate-disodium fumarate mixture etc.), gluconate buffers (e.g., gluconic acid-sodium glyconate mixture, gluconic acid-sodium hydroxide mixture, gluconic acid-potassium gluconate mixture etc.), oxalate buffers (e.g., oxalic acid-sodium oxalate mixture, oxalic acid-sodium hydroxide mixture, oxalic acid-potassium oxalate mixture etc.), lactate buffers (e.g., lactic acid-sodium lactate mixture, lactic acid-sodium hydroxide mixture, lactic acid-potassium lactate mixture etc.) and acetate buffers (e.g., acetic acid-sodium acetate mixture, acetic acid-sodium hydroxide mixture etc.). Phosphate buffers, carbonate buffers, histidine buffers, trimethylamine salts, such as Tris, HEPES and other such known buffers can be used.

Preservatives may be added to retard microbial growth, and may be added in amounts ranging from 0.2%-1% (w/v). Suitable preservatives for use with the present invention include phenol, benzyl alcohol, m-cresol, octadecyldimethylbenzyl ammonium chloride, benzyaconium halides (e.g., chloride, bromide and iodide), hexamethonium chloride, alkyl parabens, such as, methyl or propyl paraben, catechol, resorcinol, cyclohexanol and 3-pentanol.

Isotonicifiers are present to ensure physiological isotonicity of liquid compositions of the instant invention and include polhydric sugar alcohols, preferably trihydric or higher sugar alcohols, such as glycerin, erythritol, arabitol, xylitol, sorbitol and mannitol. Polyhydric alcohols can be present in an amount of between about 0.1% to about 25%, by weight, preferably 1% to 5% taking into account the relative amounts of the other ingredients.

Stabilizers refer to a broad category of excipients which can range in function from a bulking agent to an additive which solubilizes the therapeutic agent or helps to prevent denaturation or adherence to the container wall. Typical stabilizers can be polyhydric sugar alcohols; amino acids, such as arginine, lysine, glycine, glutamine, asparagine, histidine, alanine, ornithine, L-leucine, 2-phenylalanine, glutamic acid, threonine etc.; organic sugars or sugar alcohols, such as lactose, trehalose, stachyose, arabitol, erythritol, mannitol, sorbitol, xylitol, ribitol, myoinisitol, galactitol, glycerol and the like, including cyclitols such as inositol; polyethylene glycol; amino acid polymers; sulfur containing reducing agents, such as urea, glutathione, thioctic acid, sodium thioglycolate, thioglycerol, α-monothioglycerol and sodium thiosulfate; low molecular weight polypeptides (i.e., <10 residues); proteins, such as human serum albumin, bovine serum albumin, gelatin or immunoglobulins; hydrophilic polymers, such as polyvinylpyrrolidone, saccharides, monosaccharides, such as xylose, mannose, fructose or glucose; disaccharides, such as lactose, maltose and sucrose; trisaccharides, such as raffinose; polysaccharides, such as, dextran and so on. Stabilizers can be present in the range from 0.1 to 10,000 w/w per part of biopolymer.

Additional miscellaneous excipients include bulking agents, (e.g., starch), chelating agents (e.g., EDTA), antioxidants (e.g., ascorbic acid, methionine or vitamin E) and cosolvents.

As used herein, the term "surfactant" refers to organic substances having amphipathic structures, namely, are composed of groups of opposing solubility tendencies, typically an oil-soluble hydrocarbon chain and a water-soluble ionic group. Surfactants can be classified, depending on the charge of the surface-active moiety, into anionic, cationic and non-ionic surfactants. Surfactants often are used as wetting, emulsifying, solubilizing and dispersing agents for various pharmaceutical compositions and preparations of biological materials.

Non-ionic surfactants or detergents (also known as "wetting agents") may be added to help solubilize the therapeutic agent, as well as to protect the therapeutic protein against agitation-induced aggregation, which also permits the formulation to be exposed to shear surface stresses without causing denaturation of the protein. Suitable non-ionic surfactants include polysorbates (20, 80 etc.), polyoxamers (184, 188 etc.), Pluronic® polyols and polyoxyethylene sorbitan monoethers (TWEEN-20®, TWEEN-80® etc.). Non-ionic surfactants may be present in a range of about 0.05 mg/ml to about 1.0 mg/ml, preferably about 0.07 mg/ml to about 0.2 mg/ml.

As used herein, the term, "inorganic salt," refers to any compound, containing no carbon, that results from replacement of part or all of the acid hydrogen or an acid by a metal or a group acting like a metal, and often is used as a tonicity adjusting compound in pharmaceutical compositions and preparations of biological materials. The most common inorganic salts are NaCl, KCl, $NaH_2PO_4$ etc.

The present invention provides liquid formulations of a biopolymer having a pH ranging from about 5.0 to about 7.0, or about 5.5 to about 6.5, or about 5.8 to about 6.2, or about 6.0, or about 6.0 to about 7.5, or about 6.5 to about 7.0.

The instant invention encompasses formulations, such as, liquid formulations having stability at temperatures found in a commercial refrigerator and freezer found in the office of a physician or laboratory, such as from about −20° C. to about 5° C., said stability assessed, for example, by microscopic analysis, for storage purposes, such as for about 60 days, for about 120 days, for about 180 days, for about a year, for about 2 years or more. The liquid formulations of the present invention also exhibit stability, as assessed, for example, by particle analysis, at room temperatures, for at least a few hours, such as one hour, two hours or about three hours prior to use.

Examples of diluents include a phosphate buffered saline, buffer for buffering against gastric acid in the bladder, such as citrate buffer (pH 7.4) containing sucrose, bicarbonate buffer (pH 7.4) alone, or bicarbonate buffer (pH 7.4) containing ascorbic acid, lactose, or aspartame. Examples of carriers include proteins, e.g., as found in skim milk, sugars, e.g., sucrose, or polyvinylpyrrolidone. Typically these carriers would be used at a concentration of about 0.1-90% (w/v) but preferably at a range of 1-10% (w/v).

The formulations to be used for in vivo administration must be sterile. That can be accomplished, for example, by filtration through sterile filtration membranes. For example, the formulations of the present invention may be sterilized by filtration.

The biopolymer composition will be formulated, dosed and administered in a manner consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the biopolymer to be administered will be governed by such considerations, and can be the minimum amount necessary to prevent, ameliorate or treat a disorder of interest. As used herein, the term "effective amount" is an equivalent phrase refers to the amount of a therapy (e.g., a prophylactic or therapeutic agent), which is sufficient to reduce the severity and/or duration of a disease, ameliorate one or more symptoms thereof, prevent the advancement of a disease or cause regression of a disease, or which is sufficient to result in the prevention of the development, recurrence, onset, or progression of a disease or one or more symptoms thereof, or enhance or improve the prophylactic and/or therapeutic effect(s) of another therapy (e.g., another therapeutic agent) useful for treating a disease. For example, a treatment of interest can increase the use of a joint in a host, based on baseline of the injured or diseases joint, by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%. In another embodiment, an effective amount of a therapeutic or a prophylactic agent of interest reduces the symptoms of a disease, such as a symptom of arthritis by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%. Also used herein as an equivalent is the term, "therapeutically effective amount."

Where necessary, the composition may also include a solubilizing agent and a local anesthetic such as lidocaine or other "caine" anesthetic to ease pain at the site of the injection.

Generally, the ingredients are supplied either separately or mixed together in unit dosage form, for example, as a dry lyophilized powder or water-free concentrate in a sealed container, such as an ampule or sachet indicating the quantity of active agent. Where the composition is to be administered by infusion, it can be dispensed with an infusion bottle containing sterile pharmaceutical grade water or saline. Where the composition is administered by injection, an ampule of sterile water for injection or saline can be provided, for example, in a kit, so that the ingredients may be mixed prior to administration.

An article of manufacture containing materials useful for the treatment of the disorders described above is provided. The article of manufacture comprises a container and a label. Suitable containers include, for example, bottles, vials, syringes and test tubes. The containers may be formed from a variety of materials such as glass or plastic. The container holds a composition which is effective for preventing or treating, for example, a wound or a joint disease and may have a sterile access port (for example, the container may be a vial having a stopper pierceable by a hypodermic injection needle). The label on or associated with the container indicates that the composition is used for treating the condition of choice. The article of manufacture may further comprise a second container comprising a pharmaceutically acceptable buffer, such as phosphate-buffered saline, Ringer's solution and dextrose solution. It may further include other materials desirable from a commercial and user standpoint, including buffers, diluents, filters, needles, syringes and package inserts with instructions for use.

Biologically active agents and other additives may be incorporated into the cross-linked synthetic polymer composition by admixture or added to a reagent preparation. Alternatively, the agents may be incorporated into the cross-linked polymer matrix by binding these agents to the functional groups on the polymers of interest. Such compositions may include linkages that can be easily biodegraded, for example as a result of enzymatic degradation, resulting in the release of the active agent or additive into the target tissue, where it will exert its desired therapeutic effect.

A simple method for incorporating biologically active agents containing nucleophilic groups into the cross-linked polymer composition involves mixing the active agent with a polyelectrophilic component prior to addition of the polynucleophilic component. By varying the relative molar amounts of the different components of the reactive composition, it is possible to alter the net charge of the resulting cross-linked polymer composition, in order to prepare a matrix for the delivery of a charged compound such as a protein or ionizable drug. As such, the delivery of charged proteins or drugs, which would normally diffuse rapidly out of a neutral carrier matrix, can be controlled.

For example, if a molar excess of a component that is polynucleophilic is used, the resulting matrix may have a net positive charge and can be used to ionically bind and deliver negatively charged compounds. Examples of negatively charged compounds that can be delivered from these matrices include various drugs, cells, proteins, and polysaccharides.

If a molar excess of a component that is polyelectrophilic is used, the resulting matrix has a net negative charge and can be used to ionically bind and deliver positively charged compounds. Examples of positively charged compounds that can be delivered from these matrices include various drugs, cells, proteins, and polysaccharides.

The cross-linked polymer matrix compositions of the present invention can also be used to deliver various types of living cells or genes to a desired site of administration to form new tissue. The term "genes" as used herein is intended to encompass genetic material from natural sources, synthetic nucleic acids, DNA, antisense DNA and RNA.

For example, mesenchymal stem cells can be delivered using polymer matrices to produce cells of the same type as the tissue into which they are delivered. Mesenchymal stem cells may not differentiated and therefore may differentiate to form various types of new cells due to the presence of an active agent or the effects (chemical, physical, etc.) of the local tissue environment. Examples of mesenchymal stem cells include osteoblasts, chondrocytes and fibroblasts. For example, osteoblasts can be delivered to the site of a bone defect to produce new bone; chondrocytes can be delivered to the site of a cartilage defect to produce new cartilage; fibroblasts can be delivered to produce collagen wherever new connective tissue is needed; neurectodermal cells can be delivered to form new nerve tissue; epithelial cells can be delivered to form new epithelial tissues, such as liver, pancreas etc.

The cells may be either allogeneic or xenogeneic in origin. The compositions can be used to deliver cells of species that are genetically modified.

In some embodiments, the compositions of the invention may not easily be degraded in vivo. Thus, cells entrapped within the cross-linked polymer matrix compositions will be isolated from the host cells and, as such, will not provoke or will delay an immune response in the host.

To entrap the cells or genes within a cross-linked polymer matrix, the cells or genes may, for example be pre-mixed with a reagent composition or optionally with a mixture prior to forming a cross-linked polymer matrix, thereby entrapping the cells or genes within the matrix.

In a general method for effecting treating of an articulating surface or a disk or a joint, in the spine and so on within the body of a mammalian subject, the components of the reactive composition are infused to the site in need of treatment. The present invention may be prepared to include an appropriate vehicle for this injection, implantation, infusion or direction. Once at the body site of interest, the imidated biologically compatible polymer reacts with and becomes fixed to a surface, such as a tissue or a prosthesis. Thus, the imidated polymer is "biologically anchored" to the host tissue and can then react with other surfaces or polymers, such as the bridging molecule of interest.

The polymer matrix, alternatively, may be formed semisolid or as a solid object implantable in an anatomic area, or as a film or mesh that may be used to cover a segment of an area or surface. A variety of techniques for implanting solid objects in relevant anatomic areas will be likewise familiar to the artisan.

In some embodiments, compositions disclosed herein may be positioned in a surgically created defect that is to be reconstructed, and is to be left in that position after the reconstruction has been completed. The present invention may be suitable for use with local tissue reconstructions, pedicle flap reconstructions, corneal flap sealings or free flap reconstructions.

In some embodiments, this invention is directed to kits for bringing tissues or tissue parts into proximity, such as for sealing or healing.

The kits disclosed herein will include a container means for an imidated polymer of interest. The kit may include a delivery device. The kit optionally will include a container means for a second polymer of interest. Instructions for their use can be included.

Uses for such kits include, for example, therapeutic applications. The invention provides kits for use in treating a disease or condition. For example, the kit may comprise an imidated biologically compatible polymer, such as, imidated chondroitin sulfate, and a biocompatible polymer or a compound comprising an amine moiety, such as, PEG-amine.

In certain embodiments, a polymer of interest can be formed into desired structures, such as films, foams, scaffolds or other three-dimensional structures of interest. In such circumstances, other materials may be incorporated into subject compositions, in addition to one or more biologically active agents. For example, plasticizers and stabilizing agents known in the art may be incorporated in compositions of the present invention. The solid structure can be a component of a kit. Thus, an imidated biologically compatible polymer of interest may be applied to a biological surface as a solid structure and enabled to react with the biological surface. The bridging molecule then can be brought into proximity with the affixed biologically compatible polymer to react therewith.

In other embodiments, the biologically compatible polymer is used without the bridging molecule. Thus, the imidated biologically compatible polymer is used as an adhesive. The polymer can be applied in liquid form to a biological surface of interest. Alternatively, the polymer can be combined with an inert structure, which can provide support or serve as a carrier for the polymer, such as a backing for an adhesive bandage, or with a structure or device having a desired function.

The imidated polymer of interest can be exposed to a first and a second tissue and allowed to react therewith simultaneously. The imide groups react with functional groups on a tissue, such as the amino groups of protein lysines.

In another embodiment, the imide or one of the imides or the other functional group is reactive not with a tissue but with another substance for use in a body, such as a prosthesis, a hydrogel, a scaffold, a matrix and so on. Thus, the functionalized polymer of interest can be used to secure that substance to a tissue or to a particular site in a body.

The compositions disclosed herein may be used in any number of tissue repair applications, such as, but not limited to, seroma and hematoma prevention, skin and muscle flap attachment, repair and prevention of endoleaks, aortic dissection repair, lung volume reduction, neural tube repair, sealing of corneal incisions, reattaching a retina and the making of microvascular and neural anastomoses.

In one embodiment, the repair of damaged tissue may be carried out within the context of any standard surgical process allowing access to and repair of the tissue, including open surgery and laparoscopic techniques. Once the damaged tissue is accessed, a composition of the invention is placed in contact with the damaged tissue along with any surgically acceptable patch or implant, if needed. When used to repair lacerated or separated tissue, such as by joining two or more tissue surfaces, for example, following a surgical procedure, the composition may be applied to one or more of the tissue surfaces and then the surfaces are placed in contact with each other and adhesion occurs therebetween.

When used to repair herniated tissue, a surgically acceptable patch can be attached to the area of tissue surrounding the herniated tissue so as to cover the herniated area, thereby reinforcing the damaged tissue and repairing the defect. When attaching the patch to the surrounding tissue, a composition of the invention may be applied to either the patch, to the surrounding tissue, or to the patch after the patch has been placed on the herniated tissue. Once the patch and tissue are brought into contact with each other, adhesion may occur therebetween.

The surfaces to be adhered may be held together manually, or using other appropriate means, such as adhesive tape, a temporary suture and so on, while the cross-linking reaction is proceeding to completion. Cross-linking is typically sufficiently complete for adhesion to occur within about 5 to 60 seconds after mixing the components of the adhesive composition unless delayed setting is desired. However, the time required for complete cross-linking to occur is dependent on a number of factors, including the type and molecular weight of each reactive component, the degree of functionalization, and the concentration of the components in the cross-linkable compositions (e.g., higher component concentrations result in faster cross-linking times).

In one embodiment the compositions of the present invention are delivered to the site of administration using an apparatus that allows the components to be delivered separately, for example, sequentially or simultaneously. Such delivery systems may involve a multi-compartment spray device.

Alternatively, the components can be delivered separately using any type of controllable extrusion system, or they can be delivered manually in the form of separate pastes, liquids or dry powders, and mixed together manually at the site of administration. Many devices that are adapted for delivery of multi-component tissue sealants/hemostatic agents are well known in the art and can also be used in the practice of the present invention.

Yet another way of delivering the compositions of the present invention is to prepare the reactive components in inactive form as either a liquid or powder. Such compositions can then be activated after application to the tissue site, or immediately beforehand, by hydrating or applying an activator, for example. In one embodiment, the activator is a buffer solution having a pH that will activate the composition once mixed therewith. Still another way of delivering the compositions is to prepare preformed sheets, and apply the sheets as such to the site of administration. One of skill in the art can easily determine the appropriate administration protocol to use with any particular composition having a known gel strength and gelation time The compositions described herein can be used for medical conditions that require a coating or sealing layer to prevent the leakage of gases, liquid or solids. The method entails applying reagent(s) to the damaged tissue or organ to seal 1) vascular and/or other tissues or organs to stop or minimize the flow of blood; 2) thoracic tissue to stop or minimize the leakage of air; 3) gastrointestinal tract or pancreatic tissue to stop or minimize the leakage of fecal or tissue contents; 4) bladder or ureters to stop or minimize the leakage of urine; 5) dura to stop or minimize the leakage of CSF; and 6) skin or serosal tissue to stop the leakage of serosal fluid. These compositions may also be used to adhere tissues together such as small vessels, nerves or dermal tissue. The material can be used 1) by applying it to the surface of one tissue and then a second tissue may be rapidly pressed against the first tissue or 2) by bringing the tissues in close juxtaposition and then applying the material. In addition, the compositions can be used to fill spaces in soft and hard tissues that are created by disease or surgery.

For example, polymer matrix compositions of the invention can be used to block or fill various lumens and voids in the body of a mammalian subject. The compositions can also be used as biosealants to seal fissures or crevices within a tissue or structure (such as a vessel), or junctures between adjacent tissues or structures, to prevent leakage of blood or other biological fluids.

The compositions can also be used as a large space-filling device for organ displacement in a body cavity during surgical or radiation procedures, for example, to protect the intestines during a planned course of radiation to the pelvis.

The compositions of the invention can also be coated onto the interior surface of a physiological lumen, such as a blood vessel or Fallopian tube, thereby serving as a sealant to prevent restenosis of the lumen following medical treatment, such as, for example, balloon catheterization to remove arterial plaque deposits from the interior surface of a blood vessel, or removal of scar tissue or endometrial tissue from the interior of a Fallopian tube. A thin layer of the reaction mixture is preferably applied to the interior surface of the vessel (for example, via catheter) immediately following mixing of the first and second synthetic polymers. Because the compositions of the invention are not readily degradable in vivo, the potential for restenosis due to degradation of the coating is minimized.

The compositions of the invention can also be used for augmentation of soft or hard tissue within the body of a mammalian subject. Examples of soft tissue augmentation applications include sphincter (e.g., urinary, anal, esophageal) augmentation and the treatment of rhytids and scars. Examples of hard tissue augmentation applications include the repair and/or replacement of bone and/or cartilaginous tissue.

The invention now being generally described, it will be more readily understood by reference to the following examples which are included merely for purposes of illustration of certain aspects and embodiments of the present invention, and are not intended to limit the invention.

Example 1

Donor corneoscleral rims not suitable for transplantation are obtained. Corneas are preserved under standard eye bank conditions in Optisol-GS medium (Bausch & Lomb Surgical, Inc, San Dimas, Calif.) at 4° C. The procedure is performed no longer than 10 days after death, as taught in Reyes et al., Invest. Ophthal. Vis. Sci. 46(4)1247 (2005), who reported on the use of an aldehyde derivatized chondroitin sulfate with polyvinylalcohol to seal corneal incisions. However, the toxicity of those reagents was not determined.

A manual microkeratome (LSK One; Moria USA, Doylestown, Pa.) is used to perform a hinged-flap keratectomy just past the central opening of the chamber, in a way that a large hinge is obtained. This opening is similar to an artificial non-dilated pupil, which could be the reference point in a clinical setting. A 300 µm head thickness is used in all corneas. An artificial anterior chamber (ALTK System; Moria USA) is used to support the corneoscleral rims, as known in the art. The gearless tracks on the base plate of the artificial anterior chamber are designed to fit into the microkeratome head, so that in its pass across the cornea it maintains the same plane and direction. All discs with posterior stroma, Descemet's membrane and endothelial cell layer are obtained using a 6.25 mm freehand trephine.

Infusion of isotonic sodium chloride is released before the corneoscleral rims are placed on the base of the anterior chamber to clear the residual air from both the infusion line and underneath the cornea. The solution bottle is raised 1.5 m above the level of the chamber to obtain adequate intrachamber pressures (60-70 mm Hg) for the microkeratome pass. Corneas are centered according to circular guides in the base of the chamber. Mechanical epithelial scraping is performed with a 2.5 mm straight, rounded tip crescent knife (Beaver, Becton Dickinson Surgical Systems, Franklin Lakes, N.J.) to avoid surface irregularities due to loose epithelium, which may introduce errors in pachymetric and videokeratographic measurements.

The artificial anterior chamber is set to achieve a maximal flap diameter in all cases. The maneuver is intended to leave as much area in the stromal bed as possible for performing the trephination and suturing of the flap. The surgeries are all performed by the same surgeon to avoid variability related to different surgeons, using a surgical microscope (Ophthamic 900S; Moeller-Wedel, Hamburg, Germany).

Several drops of proparacaine hydrochloride are applied to the corneal surface prior to the microkeratome pass to resemble clinical conditions. A partial flap keratectomy is performed by passing the microkeratome head with its oscillating blade at a relatively constant speed across the plate stopping just past the central opening of the chamber. This approach differs from previously published techniques, in an attempt to obtain a wide flap hinge with a relatively less likelihood of flap slippage, so that more stability to the corneal flap is added and the corneal opening is reduced. The remaining stroma underneath the flap hinge is severed using a 2 mm wide Culler iris spatula (Sparta Surgical Corporation, Concord, Calif.), as to leave adequate space to perform a central trephination. Intrachamber pressure is returned to 18 to 20 mmHg by lowering the height of the isotonic sodium chloride solution bottle to 25 cm above the cornea level, and the trephine is centered according to the keratectomy and "pupillary" edge provided artificially by the central opening of the chamber. A hand trephine of 6.25 mm in diameter is used to perform a circular cut of the stromal bed. The trephine blade is carefully rotated until perforation, and the remaining circular cut is completed with corneal scissors. Donor buttons are placed in the recipient beds, left unsutured, and the flap repositioned.

The experiment consists of two groups of four corneas each. In one group (Group 1), the flap is secured with five interrupted sutures (10-0 Nylon, Sharpoint Surgical Specialties Corporation, Reading, Pa.). The suturing technique is the same in all corneas to ensure consistency.

In the second group (Group 2), the flap is secured using a tissue adhesive based on imidated chondroitin sulfate and PEG amine.

The bridging component, 10% PEG-amine, is used to overlay the CS-I. The PEG also is intentionally stained blue with a biocompatible dye (Cibacron Blue; Sigma-Aldrich). Staining the bridging component permits direct observation of the polymerized glue relative to the incision and ensures that the glue does not gain entry into the anterior chamber.

A 2.5-mm, straight, rounded-tip, crescent knife (Beaver; BD Surgical Systems) is used to apply the CS-imide to the wound margins. A thin layer is used to coat the surface of the incision and the internal wound lip. With a second crescent knife, a thin layer of bridging component of the adhesive (PEG-amine) is then applied over the first layer. The two components are allowed to polymerize for 30 seconds. Once the glue solidifies, saline is infused.

In both groups, the transplanted disc is left without sutures or glue, as it tends to keep in place by surface tension after the intrachamber pressure reaches 15-18 mmHg.

After epithelium removal, the isotonic sodium chloride infusion is closed, and corneal thickness is measured using an ultrasound pachymeter (Pach IV, Accutome Inc, Malvern, Pa.) in the center of the cornea. A second measurement is made after the hinged flap is created and reflected from the stromal bed. Central flap thickness is then calculated.

For surface curvature analysis, a commercial videokeratoscope (EyeSys Laboratories, Inc, Houston, Tex.) is used. The Placido disc is placed in a vertical position and the chamber centered according to the monitor control. Care is taken to preserve the orientation in preoperative and postoperative recordings. Three measurements are performed preoperatively and postoperatively for each cornea.

To assess graft stability, intrachamber pressure is raised progressively. Presence of leakage is monitored and pressure is recorded by a digital manometer (Digimano 1000, Netech Corp., Hicksville, N.Y.).

Calculations are made using StatsDirect, version 1.9.0, for Windows (CamCode, Ashwell, England). Mean, SD, minimum and maximum values are described.

The tissue adhesive produces good sealing and less astigmatism than other reports of microkeratome-assisted posterior lamellar keratoplasty. Furthermore, the absence of sutures makes the technique simple and considerably less time consuming.

The composition of the instant invention can be used to adhere two separated surfaces, at least one of which is a biological surface. Thus, the instant composition can be used to seal a wound or an opening by bringing the open edges together in juxtaposition. The sealing can be long term or can be short term based on the level of biodegradability of the components of the instant adhesive. A short term seal can provide a suitable time for a healing or a natural sealing of the opening to occur. Alternatively, the adhesive of interest can be used to adhere a non-biological but biocompatible surface to a biological surface. Such a non-biological surface can be found, for example, on a prosthesis, a medical device and so on.

Example 2

The method of CS-NHS synthesis using carbodiimide was as known in the art. The imide derivative significantly improved efficacy and biocompatibility. A CS-amine to act as the amine donor also was synthesized. For example, an about 3:3:1 ratio of CS, succinimide and diimide, respectively can be reacted in a small volume of saline for a short period of time. A suitable ratio of the three reagents can be about 75:100:38, as a design choice.

In another embodiment, CS (750 mg) was dissolved in 6 mL PBS (phosphate buffered saline). 1-Ethyl-3-[3-dimethylamino-propyl]carbodiimide (EDC, 1.572 g, 8.2 mmol) was dissolved in 1.5 mL PBS. A 3.3 mmol solution of N-hydroxysuccinimide (NHS) was made by dissolving 380 mg in 1.5 mL PBS. The NHS solution and the EDC were added to the CS solution, vortexed, and allowed to react for 10 minutes at 37° C. The reaction was then chilled for 30 min at −80° C. and precipitated with ethanol. The solution was then centrifuged for 5 min and the supernatant was removed and washed.

Crosslinked CS networks were synthesized with varying ratios of NHS:$NH_2$ as listed in the Table below. Polymer solutions with a concentration of 10% (w/v) were made with 1:1, 1:2 and 2:1 ratios of CS-NHS to PEG-$(NH_2)_6$. PEG-$(NH_2)_6$ and CS-NHS were dissolved in DMEM to yield 3 different concentrations: 13.3%, 10% and 6.67% (w/v). CS-NHS (50 µL) was added to a mold followed by the addition of 50 µL PEG-$(NH_2)_6$ and mixing. After 10 minutes, the networks were removed from the molds and transferred to PBS for swelling ratio measurements.

| Description | 50 µL CS-NHS (% w/v) | 50 µL PEG-amine (% w/v) |
|---|---|---|
| 1:1 CS-NHS:PEG-amine | 10 | 10 |
| 1:2 CS-NHS:PEG-amine | 6.67 | 13.3 |
| 2:1 CS-NHS:PEG-amine | 13.3 | 6.67 |

The crosslinked networks were then evaluated with respect to swelling and cytocompatibility (cells encapsulated in the networks or cultured adjacent). The swelling properties are critical to ocular adhesive applications since excess swelling can open the sealed wound or cause stigmatism. The networks were created with and without encapsulated cells. The potential delivery of cells within the adhesive has applicability for larger corneal wounds that require some new tissue formation in addition to sealing of the wound. The CS networks were comparable to the PEG control networks in all reports.

Fibroblasts were encapsulated in a CS-PEG amine network at varying ratios, 1:1, 1:2 and 2:1. Control PEG networks were produced at a concentration of 5%, 10% and 20% w/v. Cells were stained for viability using a commercially available kit. The amount of live cells in all gels was comparable, indicating the CS-I based gels were biocompatible.

In another experiment, the CS-NHS and armed PEG were dissolved in PBS carrying differing amounts of HEPES buffer, for example, 10 mM, 100 mM, 500 mM and 1000 mM HEPES. The reagents were mixed until gelation occurred and pipetting of the reagents was no longer possible. It was noted that gelation time plateaued at about 100 mM HEPES. A slight decrease in gel volume was noted with increasing HEPES concentration suggesting increasing crosslinking with increasing HEPES concentration. Modulus, or gel stiffness, generally, also increased with increasing HEPES concentration. At 500 mM, the modulus retreated a small amount, with a greater standard error.

Cells from nucleus pulposus, annulus fibrosus, chondrocytes, keratocytes, cornea endothelial cells, cornea epithelia cells and mesenchymal stem cells were tested for cytotoxicity with various gels of the instant invention. Cells also were encapsulated in various gels of interest. Cells were monitored for at least over a 21 day period. As a control, cells were exposed to 5% PEG diacrylate. Gels contained a 1:2, 1:1 or 2:1 ratios of CS to PEG. Some gels contained hyaluronic acid (HA) or glucosamine (GlcN), generally a 1:1 CS to PEG gel containing an equal part of HA or GlcN. In all circumstances, cell viability was maintained over the 21 day testing period. Cornea endothelia cells on day 8 presented with a level of cell proliferation, an anti-apoptotic effect was observed.

In another set of experiments, collagen was added to the CS-PEG gels constructed as described above to a final concentration of about 0.15% (w/v). A 1.75±0.08 fold increase of modulus was observed as compared to CS-PEG gels without collagen. It was contemplated that the collagen acts as a particulate in the gel matrix and thus endows the gel with composite properties.

The primary amines of collagen may interact with the CS-NHS groups in the gel of interest. Hence, collagen may crosslink with the gel matrix via covalent bonding. Such an increase in crosslinking may lead to a decrease in adhesiveness of the gel, because of the decrease in the number of available CS-NHS groups. One approach to avoid covalent interaction between collagen and the gel matrix is to use a functionalized collagen, such as one in which the amine group is substituted, to minimize the reactivity of the amine group. For example, the amine group can be modified to contain an acetyl group, an alkyl group, and so on, as taught hereinabove. That would lead to a gel with increased modulus without sacrificing tissue adhesiveness.

Contemplated equivalents of the polymers, polymeric matrices, subunits and other compositions described herein include such materials which otherwise correspond thereto, and which have the same general properties thereof wherein one or more simple variations of substituents are made which do not adversely affect the efficacy of such molecule or composition to achieve its intended purpose. In general, the compounds of the present invention may be prepared by the methods illustrated in the general reaction schemes as, for example, described above, or by modifications thereof, using readily available starting materials, reagents and conventional synthesis procedures. In these reactions, it is also possible to make use of variants which are in themselves known, but are not mentioned here.

All publications and patents mentioned herein are hereby incorporated by reference in their entirety as if each individual publication or patent was specifically and individually indicated to be incorporated by reference.

We claim:

1. A composition comprising a hydrophilic biologically compatible first polymer, wherein the first polymer is isolated and purified chondroitin sulfate functionalized with an imide group, and at least one second hydrophilic biologically compatible polymer, wherein said second polymer comprises at least one amine group and is capable of reacting with the first polymer, the second polymer being selected from the group consisting of poly(ethylene oxide), partially or fully hydrolyzed poly(vinyl alcohol), polypropylene oxide) block copolymers, poly(vinylpyrrolidone), poly(ethyloxazoline), poly(ethylene oxide)-co-poly(propylene oxide) block copolymers, poloxamines, carboxymethyl cellulose, hydroxyalkylated cellulose, polypeptides, polysaccharides, carbohydrates, polysucrose, dextran, heparin sulphate, keratan sulfate, heparin, alginate, gelatin, collagen, albumin, ovalbumin, poly(phosphoesters), poly(lactides), poly(glycolides), poly(caprolactones), poly(amides), poly(urethanes), poly(esteramides), poly(orthoesters), poly(dioxanones), poly(acetals), poly(ketals), poly(carbonates), poly(orthocarbonates), poly(phosphazenes), poly(hydroxybutyrates), poly(hydroxyl valerates), poly(alkylene oxalates), poly(alkylene succinates), poly(malic acids), polyvinylalcoholpoly(hydroxycellulose), chitin, chitosan, and copolymers, terpolymers or combinations or mixtures thereof.

2. The composition of claim 1, wherein said first and second polymers comprise at least ten monomeric units.

3. The composition of claim 1, wherein said imide group comprises succinimide.

4. The composition of claim 1, further comprising a surface.

5. The composition of claim 4, wherein said surface comprises a prosthesis.

6. A composition comprising the composition of claim 1 and a pharmaceutically acceptable carrier, excipient or diluent.

7. The composition of claim 1, wherein hydroxyalkylated cellulose comprises hydroxyethyl cellulose and/or methylhydroxypropyl cellulose.

8. The composition of claim 1, wherein the polypropylene oxide) block copolymers are poloxamers and/or meroxapols.

* * * * *